US012312594B2

(12) United States Patent
Kopatz

(10) Patent No.: US 12,312,594 B2
(45) Date of Patent: May 27, 2025

(54) NUCLEIC ACID ORIGAMI STRUCTURE ENCAPSULATED BY CAPSID UNITS

(71) Applicant: GEZA AD LTD., Givatayim (IL)

(72) Inventor: Idit Kopatz, Tel Aviv (IL)

(73) Assignee: GEZA AD LTD., Givatayim (IL)

( * ) Notice: Subject to any disclaimer, the term of this patent is extended or adjusted under 35 U.S.C. 154(b) by 979 days.

(21) Appl. No.: 17/049,059

(22) PCT Filed: Mar. 5, 2019

(86) PCT No.: PCT/IL2019/050239
§ 371 (c)(1),
(2) Date: Oct. 20, 2020

(87) PCT Pub. No.: WO2019/207563
PCT Pub. Date: Oct. 31, 2019

(65) Prior Publication Data
US 2021/0277420 A1    Sep. 9, 2021

Related U.S. Application Data

(60) Provisional application No. 62/661,094, filed on Apr. 23, 2018, provisional application No. 62/681,107, filed on Jun. 6, 2018, provisional application No. 62/683,058, filed on Jun. 11, 2018, provisional application No. 62/745,362, filed on Oct. 14, 2018.

(51) Int. Cl.
*C12N 15/87* (2006.01)
*C07K 14/005* (2006.01)

(52) U.S. Cl.
CPC ............ *C12N 15/87* (2013.01); *C07K 14/005* (2013.01); *C12N 2710/22022* (2013.01); *C12N 2710/22023* (2013.01); *C12N 2710/22042* (2013.01)

(58) Field of Classification Search
CPC .......... C12N 15/87; C12N 2710/22022; C12N 2710/22023; C12N 2710/22042; C12N 15/10; C07K 14/005; Y02A 50/30
See application file for complete search history.

(56) References Cited

U.S. PATENT DOCUMENTS

| | | |
|---|---|---|
| 4,235,871 A | 11/1980 | Papahadjopoulos |
| 4,501,728 A | 2/1985 | Geho |
| 4,666,828 A | 5/1987 | Gusella |
| 4,683,202 A | 7/1987 | Mullis |
| 4,801,531 A | 1/1989 | Frossard |
| 4,837,028 A | 6/1989 | Allen |
| 5,019,369 A | 5/1991 | Presant |
| 5,192,659 A | 3/1993 | Simons |
| 5,272,057 A | 12/1993 | Smulson |
| 6,830,929 B1 | 12/2004 | Sandalon |
| 9,139,816 B2 | 9/2015 | Handa |
| 2008/0131928 A1 | 6/2008 | Handa |
| 2014/0030697 A1 | 1/2014 | Ploegh |

FOREIGN PATENT DOCUMENTS

| | | |
|---|---|---|
| CA | 2572129 A1 | 1/2006 |
| CN | 107281497 A | 10/2017 |
| EP | 1785433 A1 | 5/2007 |
| JP | 2009541218 A | 11/2009 |
| JP | 4734608 B2 | 7/2011 |
| JP | 5621132 B2 | 11/2014 |
| WO | 9717456 A1 | 5/1997 |
| WO | 2006046243 A1 | 5/2006 |
| WO | 2008140538 A1 | 11/2008 |
| WO | 2017118862 A1 | 7/2017 |

OTHER PUBLICATIONS

Joona Mikkila Design of protein cage-based biohybrid materials. Doctoral Thesis, 2016, Aalto University, Finland. (Year: 2016).*
Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Kopatz et al., (2019) Packaging of DNA origami in viral capsids. Nanoscale 11(21): 10160-10166.
Wang et al., (2014) Hierarchical assembly of plasmonic nanostructures using virus capsid scaffolds on DNA origami templates. ACS Nano 8(8): 7896-7904.
Seitz et al., (2023) DNA-origami-directed virus capsid polymorphism. Nat Nanotechnol. Jul. 17, 2023, pp. 1-11, doi: 10.1038/s41565-023-01443-x. XP093084726.
El-Sagheer and Brown (2010) Click chemistry with DNA. Chem Soc Rev 39(4): 1388-1405.
Fan Youjie (2013) Biomolecular recognition effect based on DNA origami. A Thesis Submitted to Ningbo University for the Master's Degree, China. Date: May 22, 2013. 51 pages. Abstract on page II.
Goldmann et al., (1999) Molecular cloning and expression of major structural protein VP1 of the human polyomavirus JC virus: formation of virus-like particles useful for immunological and therapeutic studies. J Virol 73(5): 4465-4469.
Goodchild (1990) Conjugates of oligonucleotides and modified oligonucleotides: a review of their synthesis and properties. Bioconjug Chem 1(3): 165-187.
Hagensee et al., (1993) Self-assembly of human papillomavirus type 1 capsids by expression of the L1 protein alone or by coexpression of the L1 and L2 capsid proteins. J Virol 67(1): 315-322.

(Continued)

*Primary Examiner* — Iqbal H Chowdhury
(74) *Attorney, Agent, or Firm* — Dorsey & Whitney LLP

(57) ABSTRACT

Provided are particles of nucleic acid origami structure encapsulated by at least twelve capsid units, compositions comprising the same and uses thereof for delivery of nucleic acids to target cells.

20 Claims, 22 Drawing Sheets

(56) References Cited

OTHER PUBLICATIONS

Hong et al., (2017) DNA Origami: Scaffolds for Creating Higher Order Structures. DOI: 10.1021/acs.chemrev.6b00825. Published in final version as: Chem Rev 117(20): 12584-12640.

Kolb et al., (2001) Click Chemistry: Diverse Chemical Function from a Few Good Reactions. Angew Chem Int Ed Engl 40(11): 2004-2021.

Ni et al., (2017) Chemical Modifications of Nucleic Acid Aptamers for Therapeutic Purposes. Int J Mol Sci 18(8): 1683.

Pinheiro et al., (2012) Synthetic genetic polymers capable of heredity and evolution. Science 336(6079): 341-344.

Salunke et al., (1989) Polymorphism in the assembly of polyomavirus capsid protein VP1. Biophys J 56(5): 887-900.

Sasnauskas et al., (2002) Generation of recombinant virus-like particles of human and non-human polyomaviruses in yeast *Saccharomyces cerevisiae*. Intervirology 45(4-6): 308-317.

Varizhuk et al., (2013) Synthesis of triazole-linked oligonucleotides with high affinity to DNA complements and an analysis of their compatibility with biosystems. J Org Chem 78(12): 5964-5069.

Voigt et al., (2010) Single-molecule chemical reactions on DNA origami. Nat Nanotechnol 5(3): 200-203.

Xiao Shoujun (2011) RNA nanotechnology on the rise. Chemistry of Life 2: 173-183. Machine translated abstract.

Yu Mingxia et al., (2018) Prokaryotic expression and purification of norovirus GII.6 P particles. Journal of Microbiology 2: 85-91. Machine translated abstract.

Zlotnick et al., (2015) Self-assembling virus-like and virus-unlike particles. In: Viral Nanotechnology. CRC Press. pp. 13-26.

Kler et al., (2022) Packaging of DNA Origami in Viral Capsids: Towards Synthetic Viruses. Royal Society of Chemistry. DOI: 10.1039/d2nr01316a. 8 pages Jul. 21, 2022.

Aniagyei et al., (2008) Self-assembly approaches to nanomaterial encapsulation in viral protein cages. J Mater Chem. Author manuscript; available in PMC Oct. 5, 2009. Published in final edited form as: J Mater Chem. 18(32): 3763-3774.

Burns et al., (2018) DNA Origami Inside-Out Viruses. ACS Synth Biol 7(3): 767-773.

Cadena-Nava et al., (2012) Self-assembly of viral capsid protein and RNA molecules of different sizes: requirement for a specific high protein/RNA mass ratio. J Virol 86(6): 3318-3326.

Caspar and Klug (1962) Physical principles in the construction of regular viruses. Cold Spring Harb Symp Quant Biol 27: 1-24.

Chen et al., (2005) Packaging of gold particles in viral capsids. J Nanosci Nanotechnol 5(12): 2029-2033.

Chen et al., (2006) Nanoparticle-templated assembly of viral protein cages. Nano Lett 6(4): 611-615.

Chopra et al., (2016) Electrotransfection of Polyamine Folded DNA Origami Structures. Nano Lett 16(10): 6683-6690. Abstract.

Daniel et al., (2010) Role of surface charge density in nanoparticle-templated assembly of bromovirus protein cages. ACS Nano 4(7): 3853-3860.

Dhason et al., (2012) Differential assembly of Hepatitis B Virus core protein on single- and double-stranded nucleic acid suggest the dsDNA-filled core is spring-loaded. Virology 430(1): 20-29.

Dubochet et al., (1988) Cryo-electron microscopy of vitrified specimens. Q Rev Biophys 21(2): 129-228.

Enomoto et al., (2011) In vitro reconstitution of SV40 particles that are composed of VP1/2/3 capsid proteins and nucleosomal DNA and direct efficient gene transfer. Virology 420(1): 1-9.

He et al., (2013) Hepatitis B virus capsid polymorph stability depends on encapsulated cargo size. ACS Nano 7(10): 8447-8454.

Hong et al., (2017) DNA Origami: Scaffolds for Creating Higher Order Structures. Chem Rev 117(20): 12584-12640. Abstract.

Hu et al., (2008) Packaging of a polymer by a viral capsid: the interplay between polymer length and capsid size. Biophys J 94(4): 1428-1436.

Jiang et al., (2012) DNA origami as a carrier for circumvention of drug resistance. J Am Chem Soc 134(32): 13396-13403.

Jiang et al., (2015) A Self-Assembled DNA Origami-Gold Nanorod Complex for Cancer Theranostics. Small 11(38): 5134-5141.

Kimanius et al., (2016) Accelerated cryo-EM structure determination with parallelisation using GPUs in RELION-2. Elife 5: e18722; 21 pages.

Kiviaho et al., (2016) Cationic polymers for DNA origami coating—examining their binding efficiency and tuning the enzymatic reaction rates. Nanoscale 8(22): 11674-11680.

Kler et al., (2013) Scaffold properties are a key determinant of the size and shape of self-assembled virus-derived particles. ACS Chem Biol. Author manuscript; available in PMC Dec. 20, 2014. Published in final edited form as: ACS Chem Biol 8(12): 2753-2761.

Kusters et al., (2015) Role of charge regulation and size polydispersity in nanoparticle encapsulation by viral coat proteins. J Phys Chem B 119(5): 1869-1880. Abstract.

Li et al., (2013) Electron counting and beam-induced motion correction enable near-atomic-resolution single-particle cryo-EM. Nat Methods. Author manuscript; available in PMC Dec. 1, 2013. Published in final edited form as: Nat Methods. Jun. 2013; 10(6): 584-590.

Li et al., (2017) Single Particle Observation of SV40 VP1 Polyanion-Induced Assembly Shows That Substrate Size and Structure Modulate Capsid Geometry. ACS Chem Biol. Author manuscript; available in PMC May 19, 2018. Published In final edited form as: ACS Chem Biol. May 19, 2017; 12(5): 1327-1334.

Linko V., Mikkilä J., Kostiainen M.A. (2018) Packaging DNA Origami into Viral Protein Cages. In: Wege C., Lomonossoff G. (eds) Virus-Derived Nanoparticles for Advanced Technologies. Methods in Molecular Biology, vol. 1776. Humana Press, New York, NY. https://doi.org/10.1007/978-1-4939-7808-3_18; pp. 267-277.

Mikkilä et al., (2014) Virus-encapsulated DNA origami nanostructures for cellular delivery. Nano Lett 14(4): 2196-2200.

Mukherjee et al., (2006) Redirecting the coat protein of a spherical virus to assemble into tubular nanostructures. J Am Chem Soc 128(8): 2538-2539. Abstract.

Mukherjee et al., (2007) High cooperativity of the SV40 major capsid protein VP1 in virus assembly. PLoS One 2(8): e765; 9 pages.

Patel et al., (2017) HBV RNA pre-genome encodes specific motifs that mediate interactions with the viral core protein that promote nucleocapsid assembly. Nat Microbiol 2: 17098; 10 pages.

Porterfield et al., (2010) Full-length hepatitis B virus core protein packages viral and heterologous RNA with similarly high levels of cooperativity. J Virol 84(14): 7174-7184.

Rayaprolu et al., (2017) Length of encapsidated cargo impacts stability and structure of in vitro assembled alphavirus core-like particles. J Phys Condens Matter 29(48): 484003; 12 pages.

Rothemund (2006) Folding DNA to create nanoscale shapes and patterns. Nature 440(7082): 297-302.

Saper et al., (2013) Effect of capsid confinement on the chromatin organization of the SV40 minichromosome. Nucleic Acids Res 41(3): 1569-1580.

Schaffert et al., (2016) Intracellular Delivery of a Planar DNA Origami Structure by the Transferrin-Receptor Internalization Pathway. Small 12(19): 2634-2640. Abstract.

Sun et al., (2007) Core-controlled polymorphism in virus-like particles. Proc Natl Acad Sci U S A 104(4): 1354-1359.

Wagenknecht et al., (1988) Direct localization of the tRNA—anticodon interaction site on the *Escherichia coli* 30 S ribosomal subunit by electron microscopy and computerized image averaging. J Mol Biol 203(3): 753-760. Abstract.

Wang et al., (2011) Encapsulation of gold nanoparticles by simian virus 40 capsids. Nanoscale 3(10): 4275-4282.

Wang et al., (2014) Encapsidated hepatitis B virus reverse transcriptase is poised on an ordered RNA lattice. Proc Natl Acad Sci U S A 111(31): 11329-11334.

Wang et al., (2017) The Beauty and Utility of DNA Origami. Chem 2(3): 359-382.

Wang et al., (2018) Geometric Defects and Icosahedral Viruses. Viruses 10(1): 25; 9 pages.

Zhang (2016) Gctf: Real-time CTF determination and correction. J Struct Biol 193(1): 1-12.

Zhuang et al., (2016) A Photosensitizer-Loaded DNA Origami Nanosystem for Photodynamic Therapy. ACS Nano. Author manu-

(56) References Cited

OTHER PUBLICATIONS script; available in PMC Apr. 20, 2016. Published in final edited form as: ACS Nano. Mar. 22, 2016; 10(3): 3486-3495.
Zlotnick et al., (2013) To build a virus on a nucleic acid substrate. Biophys J 104(7): 1595-1604.
Gharakhanian et al., (2005) Cys254 and Cys49/Cys87of simian virus 40 Vp1 are essential in formation of infectious virions. Virus Res 107(1): 21-25.
Li et al., (2001) Simian virus 40 Vp1 DNA-binding domain is functionally separable from the overlapping nuclear localization signal and is required for effective virion formation and full viability. J Virol 75(16): 7321-7329.
Magaldi et al., (2012) Mutations in the GM1 binding site of simian virus 40 VP1 alter receptor usage and cell tropism. J Virol 86(13): 7028-7042.
Vologodskii (2000) Circular DNA. In: Cyclic Polymers. DOI: 10.1007/0-306-47117-5_2. 35 pages.

* cited by examiner

Scalebar: 150 nm superimposition

Synthetic particle

SV40

Fig. 7A
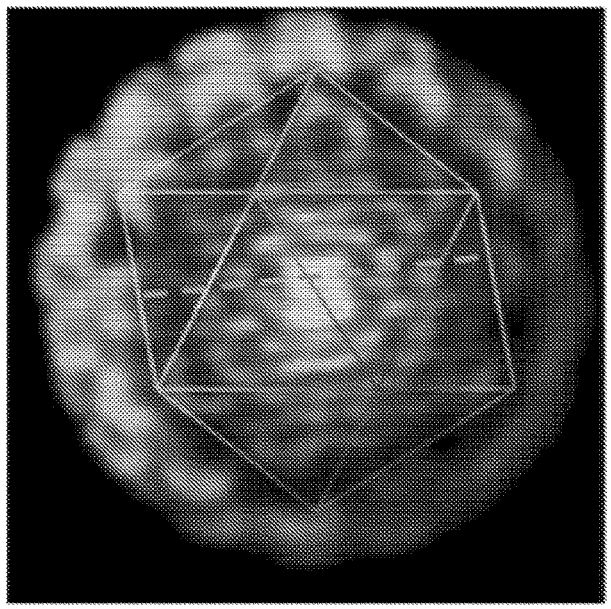
Fig. 7B
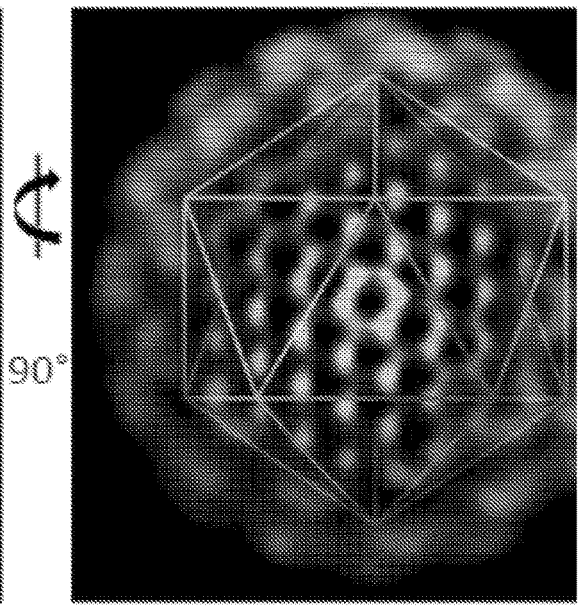
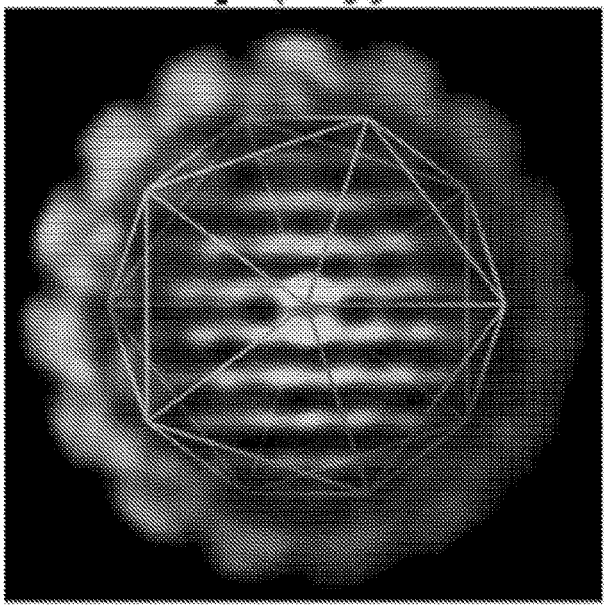
Fig. 7C

NUCLEIC ACID ORIGAMI STRUCTURE ENCAPSULATED BY CAPSID UNITS

FIELD OF INVENTION

The present invention is directed to particles of viral capsid units encapsulating nucleic acid origami structure.

BACKGROUND OF THE INVENTION

Viruses are self-replicating molecular machines that package a genome and deliver it to a host. In many cases, the shell (or capsid) of a spherical virus self-assembles around the viral genome. This is the case for simian virus 40 (SV40) that has well characterized in vitro self-assembly system.

SV40 is a small non-enveloped primate polyomavirus with a 5.2 kb double-stranded (ds) circular DNA genome. The DNA forms a minichromosome with a nucleosome structure similar to cellular chromatin. The minichromosome is enclosed in a 50 nm diameter capsid composed of 72 basic capsid subunits, pentamers of the major viral protein VP1, arranged in a T=7d icosahedral lattice. In addition to VP1, a single molecule of a minor capsid protein, VP2 or VP3, is tightly anchored to each pentamer. In the capsid, VP2 and VP3 are located internally with respect to VP1. The triangulation number T may be different for different icosahedral viruses. For example, Herpes Virus has T=16 icosahedral geometry while Adenovirus has T=25. Different triangulation numbers dictate different number of capsid subunits.

SV40 self-assembles in vitro from its basic subunits, pentamers of VP1 capsid protein, and can encapsulate any type of nucleic acid. The size and shape of in vitro assembled virus-like nanoparticle depend on the type and length of the encapsulated nucleic acid. On short single stranded (ss) RNA (≤814 nucleotides), SV40 pentamers form 22-nm diameter capsid with icosahedral T=1 geometry, composed of 12 pentamers and a single RNA molecule. With RNA or with single-stranded DNA too long to fit a T=1 particle, pentamers form strings of 22-nm particles and heterogeneous particles of 29 to 40 nm diameter which have been suggested to be of icosahedral T=3 or T=4 geometry. On a single molecule of double stranded DNA SV40 always forms 50 nm particles composed of 72 pentamers with icosahedral T=7 geometry. SV40 has also been shown to assemble in vitro around DNA from VP1 pentamers comprising VP2 or VP3 molecules (Enomoto et al. Virology 2011 420:1-9).

Due to the economy, ease of in vitro preparation, safety and lack of immunogenicity of the SV40-like nanoparticles, they hold great promise for their medical use as gene delivery vectors. However, problems exist that hinder their usefulness. One of these problems is the low compactibility of the nucleic acids, which occupy large volume compared to that of the capsid's internal cavity. The molecular mechanism of in vitro capsid assembly is based on an interplay between the stability of protein-protein interaction, and the work required to constrain the nucleic acid in the small cavity of the capsid. The flexibility and compactibility of the nucleic acid are the key factor for effective encapsulation. There are strong indications that dsDNA which is a stiff polymer and is known for its long persistence length is a poor substrate for packaging. For example, when assembling on dsDNA with Hepatitis B virus (HBV) (Dhason et al. Virology 2012, 430 (1): 20-9) or Cowpea chlorotic mottle virus (CCMV) (Mukherjee et al. Journal of the American Chemical Society 2006, 128 (8): 2538-9), aberrant non-native structures are formed, rather than a well-defined capsid with fixed size and geometry. These structures are often seen as multiplets of capsids threaded on a single nucleic acid molecule, suggesting that encapsulation of the nucleic acid is not complete. With SV40 assembled in vitro on dsDNA, small angle X-ray scattering studies indicate no electron density at the core of the particle suggesting that the DNA is excluded from the internal cavity of the capsid and that the capsids are practically empty (Saper et al. Nucleic Acids Research, 2013, 41 (3): 1569-1580). Unpackaged nucleic acid extruding out from the capsid or non-native viral structures may impede utility as a gene delivery vector.

Nevertheless, controlling the size and geometry of self-assembled capsids is not straightforward even with more flexible ssRNA substrate or ssDNA substrate. SV40 assembly on ssRNA leads to T=1 capsids or to multiplets of polymorphic capsids, instead of the native 50 nm T=7 virion sized particles (Kler and Zlotnick (ACS Chem Biol. 2013, 8 (12): 2753-61). Moreover, Cryo-EM 3D reconstruction shows that the RNA is partially extruded from the T=1 capsid (Kler and Zlotnick (ACS Chem Biol. 2013, 8 (12): 2753-61). With CCMV, efficient assembly is limited by RNA size (Cadena-Nava et al. Journal of virology 2012, 86 (6): 3318-26).

Another type of nanomaterials that can be encapsulated by self-assembly of viral capsids are nanoparticles coated with anionic ligands, such as carboxyl or citrate acidic groups (Chen et al. Journal of nanoscience and nanotechnology 2005, 5 (12): 2029-33; He et al. ACS nano 2013, 7 (10): 8447-8454; Chen et al. Nano letters 2006, 6 (4): 611-5; Wang et al. Nanoscale 2011, 3 (10): 4275-82).

Encapsulation of nanoparticles is typically simple because unlike nucleic acids, these substrates are a-priori compact. Studies of encapsulation of gold nanoparticles by Brome mosaic virus (BMV) have shown that a template with size and morphology commensurate with capsid cavity can increase assembly efficiency (Daniel at al. ACS nano 2010, 4 (7): 3853-60; Sun et al. Proceedings of the National Academy of Sciences of the United States of America 2007, 104 (4): 1354-9; Aniagyei at al. Journal of materials chemistry 2008, 18 (32): 3763-3774).

Surface charge density as well as other chemical and physical surface properties are also critical for effective encapsulation of nanoparticles (Daniel et al. ACS nano 2010, 4 (7): 3853-60; Kusters et al. The Journal of Physical Chemistry B 2015, 119 (5): 1869-1880).

DNA origami is a technology of DNA self-folding, which uses a set of short synthetic DNA oligonucleotides, called staples that mediate the folding of a long single-stranded DNA (scaffold) into a predesigned nanometric structures. The staples are designed to complement different parts of the scaffold DNA and thereby crosslink distant sections of the scaffold chain. The technique provides a platform for engineering nanometric objects with 2D and 3D geometry, with high precision and resolution. DNA origami technology has been applied to RNA and double stranded DNA scaffolds as well. DNA origami technology is used for a broad range of applications such as devices, biosensors, molecular machines and nanorobots. The ability to load chemicals and nanoparticles into DNA origami structures is exploited for therapeutic applications. Such structures have been loaded with anticancer drugs, photosensitive agents, and gold particles for chemotherapy, photodynamic and photothermal therapies.

The highly compact form of nucleic acids, produced by DNA origami technique, may allow for complete encapsulation of large nucleic acid molecules by viral capsids.

However, assembly of viral capsids around DNA origami may be challenging. The chemical and physical surface properties of DNA origami structures are different that those of the gold nanoparticles that have so far served as substrates for assembly. In addition, a unique feature of using DNA origami as a substrate for assembly is that origami structures cannot readily form perfect spheres, as compared to gold nanoparticles. A mismatch between the geometry of the nanoparticle to be encapsulated and the native capsid would make it challenging to predict the outcome of encapsulation. Consequently, this geometrical limitation may adversely affect the efficiency of encapsulation of DNA origami.

Various publications have been directed to the use of virus like particles for delivery of nucleic acids. U.S. Pat. No. 6,830,929 is directed to in-vitro construction of SV40 viruses and pseudoviruses. A publication by Zlotnick A. et. al. (Biophysical Journal, 2013, 104, 1595-1604) is entitled "To Build a Virus on a Nucleic Acid Substrate". Handa H. et. al. (Virology, 2011, 420, 1-9) is entitled "In vitro reconstitution of SV40 particles that are composed of VP1/2/3 capsid proteins and nucleosomal DNA and direct efficient gene transfer". US application publication No. US20080131928 is directed to a viral particle-like structure in physiological conditions, and method of forming it. Other publications, including Mikkila et. al. (Nano Lett. 2014, 14, 2196-2200) and Burns et. al. (ACS Synth Biol. 2018, 7, 767-773) have reported compositions of matter comprising an origami particle and viral protein.

There is still a need in the art for efficient particles that exhibit bona fide viral architecture that can completely encapsulate large nucleic acid molecules and that can effectively be used to transfer such nucleic acid molecules to cells.

SUMMARY OF THE INVENTION

The present invention, in embodiments thereof, provides particles of at least one nucleic acid origami structure encapsulated by at least twelve capsid units, compositions comprising the same and uses thereof.

According to some embodiments, the advantageous particles of the invention allow efficient delivery of nucleic acid to target cells, due to their ability to efficiently and completely encapsulate the nucleic acid, which is in the form of highly compact origami structure. The encapsulated nucleic acid, as exemplified herein, is fully encapsulated and protected within the shell that is made of capsid units, and does not protrude and is not extruded from the particle. The advantageous particles of the invention, as demonstrated herein, exhibit icosahedral viral architecture, that completely encapsulates nucleic acid and bears perfect resemblance to a virus. Further, without wishing to be bound by any theory or mechanism, the advantageous particles which, as demonstrated herein below, highly resemble a viral structure, are effective in gene delivery since the particle and the nucleic acid are trafficked and metabolized in the cells as efficiently as native viruses, which are predestined to be recognized by the cell machinery; the capsid may open up by cellular enzymatic reactions and, after the opening of the capsid, specific structures are formed to facilitate nuclear uptake of the nucleic acid cargo. In contrast, particles which do not exhibit high resemblance to a virus, are not likely to get into the nucleus very efficiently. They will likely be phagocytized by the cells but will end up in degradative organelles. Accordingly, the particles of the invention exhibit high potential for gene delivery activity.

According to some embodiments, it is disclosed herein that DNA origami can be used as a new class of substrates for capsid assembly. To achieve this aim, as exemplified herein, SV40 capsid proteins and DNA origami structure molecules, packed to near-spherical morphology and suitable diameter to best match the inner cavity of the native SV40 capsid were used. As further exemplified herein below, a particle having a shell comprising capsid units, each made from one or more capsid proteins, can assemble around a core of DNA origami structure and encapsulate it with high efficiency. In some exemplary embodiments, the cryo-EM structure of the resulting particles demonstrate that the outer shell forms a regular SV40 lattice of T=7d icosahedral symmetry. In some embodiments, as demonstrated by the cryo-EM structure, within the core of the particle (i.e., inside the shell), the structural features of the DNA origami, such as the parallel helices arranged in a "honeycomb" lattice, can be identified, indicating that the DNA origami is encapsulated within the capsid shell in its entirety.

According to some exemplary embodiments, as demonstrated herein below, the DNA origami structure and the capsid are not randomly oriented, as the axis that connects the two opposing honeycomb facets of the DNA origami structure is oriented slightly off the three-fold symmetry axis of the icosahedral capsid (for example, at an inclination angle of ~−6.8° towards the three-fold symmetry axis). Thus, advantageously, SV40-like particles form around DNA origami with high fidelity, efficiency and reproducibility, and enable to exactly reproduce the capsid and accurately position the two lattices, DNA origami and SV40 capsid, with respect to each other, to form a useful and active particle. In some embodiments, the DNA origami structure is randomly oriented with respect to the capsid.

According to some embodiments, there is provided a particle comprising a core and a shell, said core comprising at least one nucleic acid origami structure encapsulated by the shell, said shell comprising at least 12 capsid units, the capsid units comprising one or more capsid proteins.

According to some embodiments, the nucleic acid origami structure may be a single stranded DNA, double stranded DNA, any form of single stranded RNA and any form of double stranded DNA, modified nucleic acids, synthetic nucleic acids or any combination thereof and multiplicity thereof. In some embodiments, the nucleic acid origami structure may include a multiplicity of nucleic acid scaffolds or smaller origami structures, each may optionally comprise more than one type of nucleic acid.

According to some embodiments, the shell of the particle may have a quasi-spherical geometry. According to some embodiments, the shell of the particle may have an icosahedral geometry. According to some embodiments, the particle can be spherical or near spherical.

According to some embodiments, the diameter of the particle may be between about 10 and about 200 nanometers (nm). According to some embodiments, the diameter of said particle may be greater than about 20 nm.

According to some embodiments, the capsid unit may include at least five capsid proteins According to some embodiments, each of the capsid unit may include pentamers and/or hexamers of capsid proteins. In some embodiments, the capsid protein is a viral protein.

In some embodiments, the viral protein is from a virus selected from the virus family Polyomaviridae. In some embodiments, the viral protein is from a human polyomavirus. In some embodiments, the viral protein is from a virus selected from the group consisting of: SV40 virus, JC virus or BK virus. In some embodiments, the capsid protein is from SV40 virus.

According to some embodiments, the capsid protein may be selected from capsid protein VP1, capsid protein VP2, capsid protein VP3 or any combination thereof. In some embodiments, the capsid protein is VP1.

In some embodiments, the origami structure may be encapsulated by at least 72 capsid units. In some embodiments, the capsid units may include a combination of viral protein molecules selected from the group consisting of: 5 VP1 molecules, 5 VP1 molecules and one VP2 molecule, 5 VP1 molecule and one VP3 molecule, and 5 VP1 molecules and one VP2 molecule or one VP3 molecule, or any combination thereof.

In some embodiments, the particle is for use in delivering a nucleic acid molecule into a target cell. In some embodiments, the target cell is selected from an in vitro cell, or a cell harbored in a tissue or an organism.

In some embodiments, there is provided a composition comprising a plurality of the particles of the invention.

In some embodiments, there is provided a use of a particle comprising a core and a shell, said core comprising at least one nucleic acid origami structure encapsulated by the shell, said shell comprising at least 12 capsid units, the capsid units comprising one or more capsid proteins, for delivery of the nucleic acid to a cell.

In addition to the exemplary aspects and embodiments described above, further aspects and embodiments will become apparent by reference to the figures and by study of the following detailed description.

BRIEF DESCRIPTION OF THE DRAWINGS

FIG. 1A—25 nm nearly spherical origami structure built of 2873 nucleotides (nt) long single-stranded DNA; FIG. 1B—30 nm nearly spherical origami structure built of 5386 nt long single-stranded DNA; FIG. 1C—35 nm nearly spherical origami structure built of 7560 nt long single-stranded DNA; FIG. 1D—40 nm nearly spherical origami structure composed of two half spheres; one is built of 7560 nt long single-stranded DNA and the second is built of 7249 nt single stranded DNA.

FIG. 2A: Particle including VP1 assembled on nearly spherical DNA origami structure of 25 nm diameter; FIG. 2B: Particle including VP1 assembled on nearly spherical DNA origami structure of 30 nm diameter; FIG. 2C: Particle including VP1 assembled on nearly spherical DNA origami structure of 35 nm diameter; and FIG. 2D: Particle including VP1 assembled on nearly spherical DNA origami structure of 40 nm diameter. In all images, assembly products are observed along with free origami structures and free VP1 pentamers in the background.

FIG. 4A: CV1 cells treated with fluorescently-labeled naked (not packaged inside viral capsid) origami structure (construct, control). FIG. 4B: CV1 cells incubated with viral capsids assembled in vitro around DNA origami structure, showing uptake of the fluorescently labeled DNA (marked by arrows) into the cells;

FIG. 5A: Top panel—Representative cryo-EM micrograph of SV40-like particles showing a uniform population of 50-nm particles. Scale bar represents 100 nm. Inset is showing origami-filled exhibiting striped pattern (left) and empty (right) particles (enlarged in the middle panel). Bottom panel—2D class averages from total 48778 particles indicating the presence of both empty and DNA origami-filled particles;

FIG. 5B: 3D reconstruction of empty particle at 7.3 Å resolution (top panel—a front view; middle panel—an internal view), and the corresponding 2D classes of 26,110 particles (bottom panel).

FIG. 5C: 3D reconstruction of origami-filled particles at 25 Å resolution (top panel—a front view, middle panel—an internal view) and the corresponding 2D classes of 19786 particles (bottom panel).

FIG. 5D: A demonstration of icosahedral symmetry of reconstructed particle. To demonstrate the icosahedral symmetry, an icosahedron was manually fitted to the surface of the cryo-EM reconstructed origami-filled capsid by aligning its vertices to the center of the pentavalent pentamers in the shell. The five-, three- and two-fold symmetry axes are marked as pentagons, triangle and rhombus respectively on the icosahedron facets;

FIG. 5E: An illustration of the Caspar and Klug method of calculation of the icosahedral triangulation number, T. The pentagons indicate pentavalent pentamers. T is given by the rule: $T=h^{}2+hk+k^{}2$. For $T=7d$, $h=2$ and $k=1$, h represented by arrows 1 and 2 while K represented by arrow 1'. The localization of pentavalent VP1 pentamers on the reconstructed capsid corresponds to T=7d;

FIG. 6A: A schematic representation of the 35 nm DNA origami structure shown at different observation angles; FIG. 6B: 3D electron density map of 3D reconstruction of DNA origami-filled capsid. Views at varying observation angles of the DNA origami-filled capsid correspond to the respective views of the DNA origami design in FIG. 6A.

FIGS. 7A-C: pictograms showing solid representation of 3 views of the encapsulated 35 nm DNA origami with respect to the capsid-aligned icosahedron. The honeycomb facet of the DNA origami faces the icosahedral three-fold symmetry with a tilt (FIG. 7B). When rotated, the axis that connects two opposing honeycomb facets is seen parallel to the origami helices marked by dashed line, is located 6.8° off the icosahedron three-fold symmetry axis (FIG. 7A). FIG. 7C-shows a rotated view of FIG. 7A.

FIG. 8: Pictogram showing Electrophoretic Mobility Shift Assay (EMSA) analysis demonstrating formation of a stable VP1/DNA origami complex. 35 nm DNA origami was mixed with VP1 pentamers at a molar ratio of 400 pentamers per DNA origami structure. Assembly products were analyzed on 0.7% agarose gel and stained with EtBr. M—Size Marker, 0—origami structure (without pentamers); 400—Origami structure incubated with pentamers.

FIG. 9: Unfolding of DNA origami under intracellular conditions (37° C. and 1 mM Mg+) demonstrated by increased accessibility to the enzymatic action of the DNA polymerase.

DETAILED DESCRIPTION OF THE INVENTION

Figure 1A:
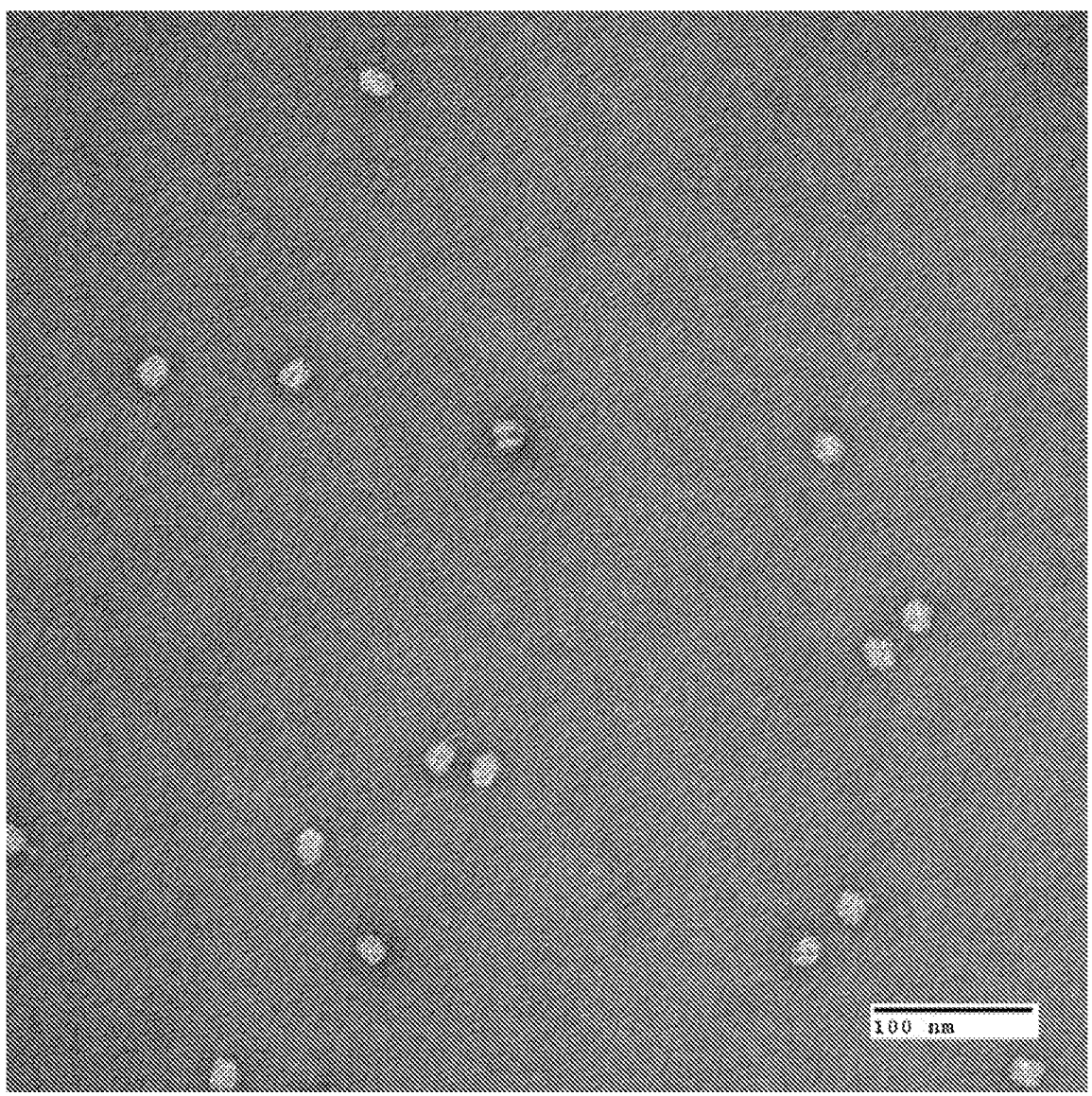
FIGS. 1A-D: Electron micrographs of near-spherical DNA origami structures of various sizes.
Figure 1B:
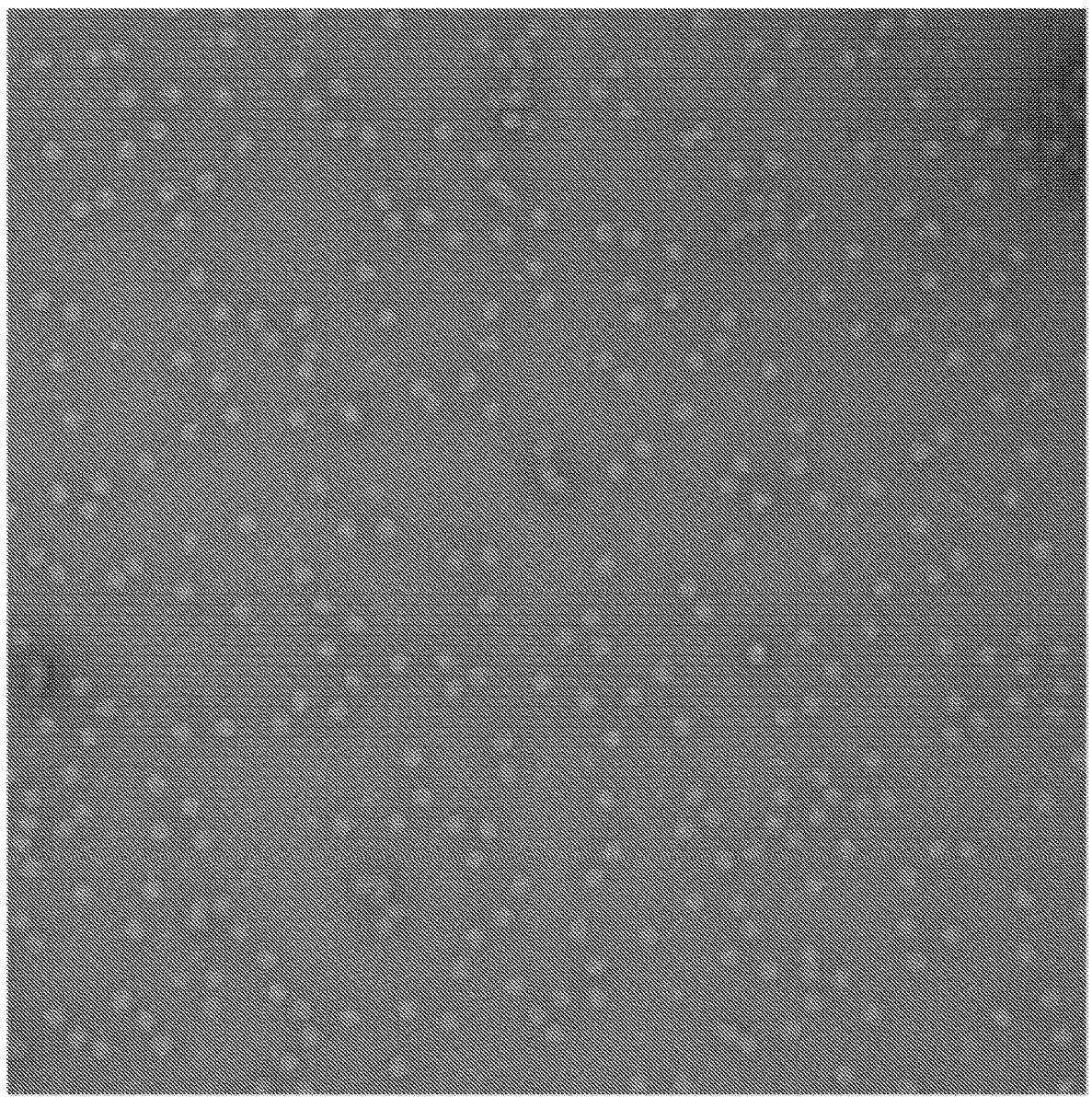
Figure 1C:
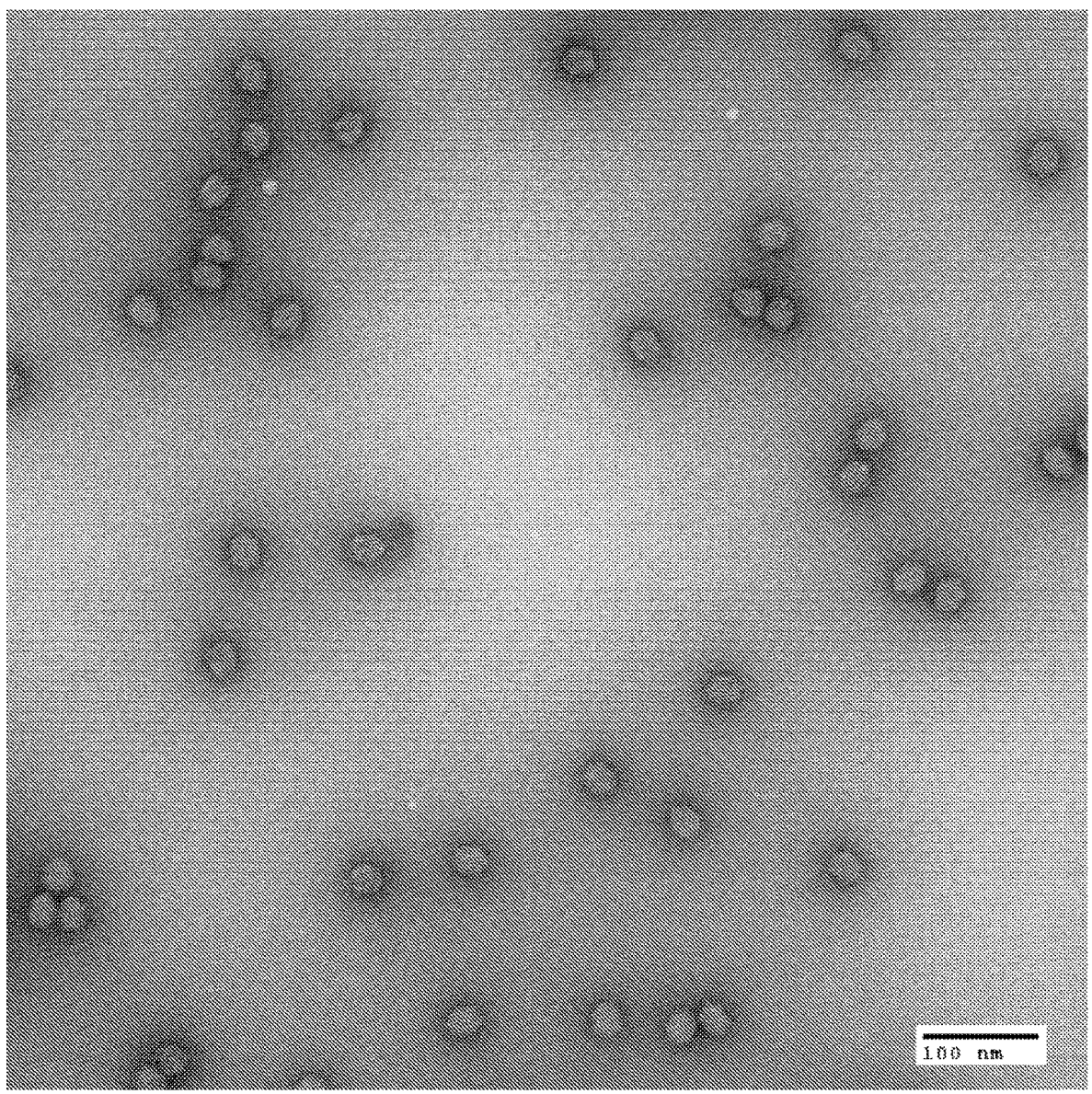
Figure 1D:
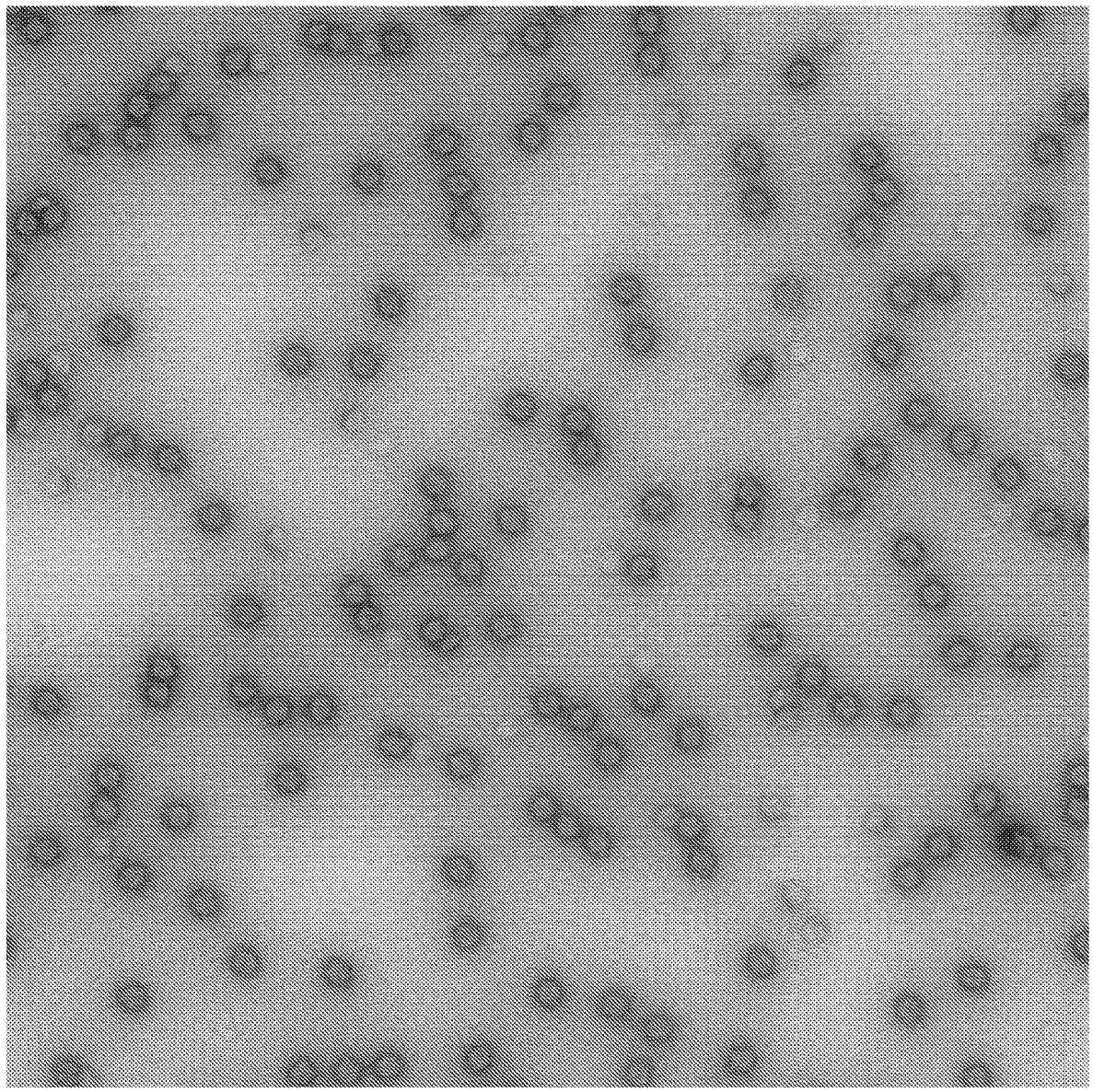

According to some embodiments, there is provided an advantageous particle comprising at least one nucleic acid origami structure encapsulated by at least 12 capsid units, the capsid units comprising one or more capsid proteins. In some embodiments, the particle has a core and a shell, wherein the shell is made of capsid units and the core includes a nucleic acid origami structure encapsulated within the shell. Further provided are compositions comprising a plurality of the particles and uses thereof for transferring/transfecting/delivering the nucleic acid encapsulated in the particles to target cells.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "nucleic acid", "nucleic acid molecules" "oligonucleotide", "polynucleotide", and "nucleotide" may interchangeably be used herein. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, Antisense RNA, and the like. Each possibility is a separate embodiment. The terms further include oligonucleotides composed of naturally occurring bases, sugars, and covalent internucleoside linkages, as well as oligonucleotides having non-naturally occurring portions, which function similarly to respective naturally occurring portions. In some embodiments, the nucleic acid is in the form of an origami structure.

Origami Structure

As used herein, the terms "nucleic acid origami structure" and "origami structure" may interchangeably be used. The terms refer to a nucleic acid molecule that has been folded on a nanoscale into a particular three-dimensional shape. Origami structures will be well known to one skilled in the art and can be produced by molecular biological techniques such as are described in Rothemund et al., 2006, Nature 440:297-302 which is herein incorporated in its entirety. Briefly, a long strand of nucleic acid (scaffold) is folded using short nucleic acid strands, also known as "staple" strands. Binding of these staple strands leads to a conformational change in the long strand, and many staple strands can be used to bring about a specific folding. Further rounds of heating and cooling are used to optimize folding and for binding and removal of the staple strands.

Origami structures already folded into specific shapes can be purchased commercially. Companies selling origami structures include, but are not limited to, tilibit nanosystems, and Eurofins Genomics.

In some embodiments, the origami structure comprises a nucleic acid strand. In some embodiments, the origami structure comprises a nucleic acid selected from the group consisting of: single stranded DNA, double stranded DNA, any form of single stranded RNA and double stranded RNA (including mRNA, shRNA, siRNA, miRNA, Antisense RNA, and the like), modified nucleic acids, synthetic nucleic acids, any combination thereof as well as multiplicity thereof. Each possibility is a separate embodiment. In some embodiments, an origami structure comprises one nucleic acid molecule. In some embodiments, an origami structure comprises more than one nucleic acid molecule. In some embodiments, an origami structure can include a combination of more than one type of nucleic acid molecules. In some embodiments, the nucleic acid is not in linear from, but is rather compacted into an origami structure. In some embodiments, an origami structure can include one or more nucleic acids scaffolds, wherein each scaffold may be comprised of one or more types of nucleic acids. For example, a scaffold can include DNA molecule linked to RNA molecule.

In some embodiments, an origami structure can include one or more smaller origami structures, wherein each smaller origami structure may be comprised of one or more types of nucleic acids. In some embodiments, the staples consist of one or more types of nucleic acids. In some embodiments, the staples and scaffold each consist of different types of nucleic acids.

An origami structure can take on any shape desired for a specific application. In some embodiments, the shape of the origami structure is selected from the group consisting of: a sphere, a cube, a pyramid, a cone, a spring and a globular shape. In some embodiments, the origami structure is configured to fill or be encapsulated by a shell. In some embodiments, the origami structure is spherical. In some embodiments, the origami structure is essentially spherical. In some embodiments, the origami structure is nearly spherical. In some embodiments, the origami structure is spherical and configured to fill a virus-like particle.

In some embodiments, the nucleic acid origami structure is capable of unfolding in a cell. In some embodiments, the nucleic acid origami structure is capable of unfolding under conditions of intracellular environment. In some embodiments, the nucleic acid origami structure is designed such that it can unfold under conditions of intracellular environment.

In some embodiments, the nucleic acid origami structure is capable of being expressed in a cell. In some embodiments, the nucleic acid template of origami structure is capable of being expressed in the cell. In some embodiments, the nucleic acid origami structure is capable of being expressed in a cell, after it has been unfolded in the cell.

In some embodiments, the nucleic acid origami structure is capable of unfolding upon being released from the protein capsid shell, after it has been introduced into a cell. In some embodiments, the nucleic acid origami structure is capable of unfolding upon being released from the protein capsid shell in an intracellular environment. In some embodiments, the nucleic acid origami structure is designed such that it can unfold when released from the protein capsid shell in the intracellular environment.

In some embodiment, the staples of the nucleic acid origami structure are capable of being disassembled in a cell, such that the nucleic acid template of the origami structure is released in the cell. In some embodiments, the disassembly of the staples of the nucleic acid origami structure are affected by intercellular conditions, such as, but not limited to: temperature, salt concentration, magnesium concentration, pH, and the like, or any combination thereof. In some embodiments, the staples of the nucleic acid origami structure are designed to disassemble in intracellular conditions of temperature and/or intracellular conditions of magnesium concentration to release the nucleic acid template of the origami structure.

In some embodiments, the staples of the nucleic acid origami structure may consist or be comprised of one or more oligonucleotides conjugated by hydrazone chemical ligation. In some embodiments, the staples of the nucleic acid origami structure may consist or be comprised of at least two oligonucleotides conjugated by hydrazone chemical ligation. In some embodiments, the staples of the nucleic acid origami structure may consist or be comprised of two oligonucleotides conjugated by hydrazone chemical ligation. In some embodiments, the staples of the nucleic acid origami structure may consist or be comprised of one or more modified oligonucleotides that may be conjugated by hydrazone chemical ligation.

In some embodiments, the staples of the nucleic acid origami structure may consist or be comprised of one or more oligonucleotides conjugated by disulfide bond. In some embodiments, the staples of the nucleic acid origami structure may consist or be comprised of at least two oligonucleotides conjugated by disulfide bond. In some embodiments, the staples of the nucleic acid origami structure may consist or be comprised of two oligonucleotides conjugated by disulfide bond. In some embodiments, the staples of the nucleic acid origami structure may consist or be comprised of one or more modified oligonucleotides that may be conjugated by disulfide bond.

In some embodiments, the staples may include, consist of or comprise of oligonucleotides conjugated by hydrazone chemical ligation, oligonucleotides conjugated by disulfide bond, or any combination thereof.

In some embodiments, the staples of the origami structure are capable of being degraded under acidic conditions of the cellular endosome and release the nucleic acid template of the origami structure. In some embodiments, the staples of origami structure are designed to degrade under acidic conditions of the cellular endosome and release the nucleic acid template of the origami structure.

In some embodiments, the staples of the origami structure are capable of being reduced in a cell, to release the nucleic acid template of origami structure. In some embodiments, the staples of the origami structure are capable of being reduced under intracellular conditions and release the nucleic acid template of origami structure. In some embodiments, the staples of the origami structure are designed to be reduced under intracellular condition and release the nucleic acid template of origami structure.

In some embodiments, the diameter of the origami sphere (or near-sphere) is between 10 and 200, 10 and 180, 10 and 160, 10 and 140, 10 and 120, 10 and 100, 10 and 80, 10 and 60, 20 and 200, 20 and 180, 20 and 160, 20 and 140, 20 and 120, 20 and 100, 20 and 80, or 20 and 60 nanometers (nm). Each possibility represents a separate embodiment of the invention. In some embodiments, the diameter of the origami sphere is between 10 and 200 nm. In some embodiments, the diameter of the origami sphere is greater than 10, 20, 22, 25, or 30 nm. Each possibility represents a separate embodiment of the invention. In some embodiments, the diameter of the origami sphere is greater than 22 nm. In some embodiments, the diameter of the origami sphere is greater than 25 nm.

In some embodiments, the distance from the center to the periphery of the origami structure is between 10 and 200, 10 and 180, 10 and 160, 10 and 140, 10 and 120, 10 and 100, 10 and 80, 10 and 60, 20 and 200, 20 and 180, 20 and 160, 20 and 140, 20 and 120, 20 and 100, 20 and 80, or 20 and 60 nanometers (nm). Each possibility represents a separate embodiment of the invention. In some embodiments, the distance from the center to the periphery of the origami structure is between 10 and 200 nm. In some embodiments, the distance from the center to the periphery of the origami structure is greater than 10, 20, 22, 25, or 30 nm. Each possibility represents a separate embodiment of the invention. In some embodiments, the distance from the center to the periphery of the origami structure is greater than 17 nm. In some embodiments, the distance from the center to the periphery of the origami structure is greater than 20 nm. In some embodiments, the distance from the center to the periphery of the origami structure is about 17 nm. In some embodiments, the distance from the center to the periphery of the origami structure is about 20 nm. In some embodiments, the distance from the center to the periphery of the origami structure is about 30 nm.

Capsid Units and Capsid Proteins

As used herein, the terms "capsid unit" or "capsid subunit" refer to a structural unit which is comprised of one or more capsid proteins, wherein "capsid" refers to a protein shell of a virus. In some embodiments, the capsid unit is a capsomer. In some embodiments, a combination of one or more capsid units form the shell of the particle of the invention. In some embodiments, a combination of twelve or more capsid units form the shell of the particle of the invention. In some embodiments, the capsid protein is of a natural source. In some embodiments, a capsid protein has at least 50%, at least 70%, at least 75%, at least 80%, at least 85%, at least 90%, at least 95%, or at least 99% sequence homology to a native viral capsid protein. Each possibility is a separate embodiment. In some embodiments, the viral protein is from a virus selected from the virus family Polyomaviridae. In some embodiments, the capsid protein is of a virus selected from the group consisting of: SV40 virus and human polyomaviruses, including, for example, JC virus or BK virus. In some embodiments, a virus of the Polyomaviridae may be selected from the group consisting of: Merkel cell polyomavirus, *Trichodysplasia spinulosa* polyomavirus, Human polyomavirus 9, Human polyomavirus 12, New Jersey polyomavirus, BK polyomavirus, JC polyomavirus, KI polyomavirus, WU polyomavirus, Human polyomavirus 6, Human polyomavirus 7, MW polyomavirus, STL polyomavirus and Lyon IARC polyomavirus. Each possibility is a separate embodiment. In some embodiments, the capsid protein is from SV40 virus. In some embodiments, the capsid protein is a modified SV40 capsid protein. In some embodiments, the capsid proteins are of artificial source. In some embodiments, an artificial capsid protein may be a modified or mutant form of known viral capsid protein. In some embodiments, artificial capsid protein may include a chimera protein derived from one or more known viral capsid proteins. In some embodiments, an artificial capsid protein may include chimera protein containing one or more domains from one or more viral capsid proteins. In some embodiments, artificial capsid protein may include non-viral regions or domains, for example an artificial protein may include non-viral sequences instead of or in addition to viral sequences or domains. In some embodiments, an artificial capsid protein may contain one or more functional domains capable of mimicking native viral capsid proteins. In some embodiments, the capsid proteins may include any modified forms or mutant forms of known capsid proteins. In some embodiments, the capsid proteins may be any modified forms or mutant forms of viral capsid proteins. In some embodiments, the capsid proteins may be modified forms or mutant forms of SV40 capsid proteins. In some embodiments, the capsid proteins may include any modified forms or mutant forms of SV40 capsid proteins. In some embodiments, the capsid proteins may be or include genetically engineered forms of known viral capsid proteins. In some embodiments, the capsid proteins may include one or more domains of known viral capsid proteins of various sources. In some embodiments, a combination of one or more types of viral capsid proteins can form a capsid unit. In some embodiments, a combination of several capsid units can form the shell of the particle. In some exemplary embodiments, the shell of the particle includes at least 12 capsid units. In some embodiments, each capsid unit may include at least one viral protein. In some embodiments, each capsid unit may include at least five viral proteins. In some embodiments, the capsid unit is a pentamer of capsid proteins. In some embodiments, the capsid units form a shell that has an icosahedral geometry. In some embodiments, the particle of the invention has an icosahedral geometry. In some embodiments, icosahedral geometry relates to a structure having 12 vertices, twofold, threefold and fivefold symmetry axes and a characteristic number of structural units defined by icosahedral triangulation number; Icosahedral triangulation number may be calculated following Caspar and Klug system (Physical principles in the construction of regular viruses. Cold Spring Harb Symp Quant Biol. 1962; 27:1-24). Icosahedral geometry may be determined based on Caspar and Klug system (Physical principles in the construction of regular viruses. Cold Spring Harb Symp Quant Biol. 1962; 27:1-24). In some embodiments, icosahedral geometry relates to capsid units that are arranged in the form of a hollow, quasi-spherical structure. In some embodiments, icosahedral capsids include capsids with geometric defects in the icosahedral lattice according to Wang and Zlotnick et al. Viruses 2018, 10:25.

In some embodiments, the term "quasi-spherical" is directed to encompass hollow structures, having an external shell surface arranged around an internal core. In some embodiments, quasi-spherical may include such geometrical shapes as: icosahedral, icosahedral with defects, non-perfect icosahedral, perfect sphere, near sphere, semi-sphere, ellipsoid, and the like.

According to some embodiments, the particle has icosahedral geometry. In some embodiments, the particle has quasi-spherical geometry. In some embodiments, the particles may be spherical, semi-spherical or near spherical.

In some embodiments, the capsid protein is a viral protein (VP). In some embodiments, the capsid protein may be selected from: capsid protein VP1 (VP1), capsid protein VP2 (VP2), capsid protein VP3 (VP3) and a combination thereof. Each possibility is a separate embodiment. In some embodiments, the capsid protein is VP1.

In some embodiments, VP1, VP2 and VP3 refer to Polyomaviridae VP1, VP2 and VP3, respectively.

In some embodiments, VP1, VP2 and VP3 refer to JC VP1, JC VP2 and JC VP3, respectively.

In some embodiments, VP1, VP2 and VP3 refer to BK VP1, BK VP2 and BK VP3, respectively.

In some embodiments, VP1, VP2 and VP3 refer to SV40 VP1, SV40 VP2 and SV40 VP3, respectively.

In some embodiments, the capsid protein is a viral protein (VP), or modified forms thereof. In some embodiments, the capsid protein may be selected from: capsid protein VP1 (VP1), and/or modified forms thereof, capsid protein VP2 (VP2) and/or modified forms thereof, capsid protein VP3 (VP3), and/or modified forms thereof, or any combination thereof. Each possibility is a separate embodiment. In some embodiments, modified forms of VP1, VP2 and VP3 refer to modified forms of Polyomaviridae VP1, VP2 and VP3, respectively In some embodiments, modified forms of VP1, VP2 and VP3 refer to modified forms of JC VP1, JC VP2 and JC VP3, respectively In some embodiments, modified forms of VP1, VP2 and VP3 refer to modified forms of BK VP1, BK VP2 and BK VP3, respectively. In some embodiments, modified forms of VP1, VP2 and VP3 refer to modified forms of SV40 VP1, SV40 VP2 and SV40 VP3, respectively.

Methods of encapsulating a nucleic acid in capsids are well known to those skilled in the art and are also provided herein below. Further texts such as Mukherjee et al, PLOS One, 2: e765 (2007) and S. Kler, et al., JACS chemical biology 8, 2753-2761 (2013) can be consulted for further guidance.

Encapsulation

As used herein, the term "encapsulated", with respect of the origami structure, is to be understood with its plain meaning, i.e., that the origami structure is completely surrounded by capsid units. In some embodiments, the origami structure is fully surrounded by the capsid units. In some embodiments, the origami structure is not exposed to exterior portions of the capsid unit. In some embodiments, the capsid units form a shell encapsulating a closed core in which the origami structure resides/harbored. In some embodiments, the origami nucleic acid is more completely encapsulated than the same nucleic acid in a less compact form would be.

In some embodiments, one origami structure is encapsulated by at least twelve capsid units. In some embodiments, more than one origami structure is encapsulated by at least twelve capsid units.

In some embodiments, the origami structure is encapsulated by a shell of at least 12, 32, 42, 72, 92, 122, 132, 162, 212, 252, 272, 282 or 312 capsid units. Each possibility represents a separate embodiment of the invention. In some embodiments, the origami structure may be encapsulated by at least 72 capsid units. In some embodiments, the origami structure is encapsulated by at least 72 capsid pentamers. In some embodiments, the capsid units of the shell may be identical or different in number or composition of the capsid proteins that make the capsid unit of native viral capsid. In some embodiments, the capsid proteins of all or some of the capsid units are all VP1 or modified/mutant forms thereof. In some embodiments, the capsid proteins of all or some of the capsid units are VP1 and VP2 or modified/mutant forms thereof. In some embodiments, the capsid proteins of all or some of the capsid units are VP1 and VP3 or modified/mutant forms thereof. In some embodiments, the capsid proteins of all or some of the capsid units are VP1, VP2 and VP3 or modified/mutant forms thereof. In some embodiments, the capsid unit may be comprised of at least five viral proteins. In some embodiments, the capsid unit may be comprised of pentamers of viral proteins. In some embodiments, the capsid unit may be comprised of pentamers of VP1 proteins. In some embodiments, the capsid unit may be comprised of pentamers of VP1 proteins that may be accompanied by one or more additional viral proteins, such as, VP2 and/or VP3. In some embodiments, the capsid unit may include a combination of viral protein molecules selected from the group consisting of: 5 VP1 molecules; 5 VP1 molecules and one VP2 molecule; 5 VP1 molecule and one VP3 molecule; 5 VP1 molecule and one VP2 molecule or one VP3 molecule, or any combination thereof. Each possibility is a separate embodiment. In some embodiments, the origami structure is encapsulated by at least 360 capsid proteins. In some embodiments, the origami structure is encapsulated by any combination of at least 72 VP1 pentamers wherein each pentamer consists of only VP1 molecules and modified forms thereof, at least 72 VP1 pentamers wherein each pentamer comprises 1 VP2 molecule and modified forms thereof, at least 72 VP1 pentamers wherein each pentamer comprises 1 VP3 molecule and modified forms thereof or at least 72 VP1 pentamers wherein each pentamer comprises 1 VP2 molecule or 1 VP3 molecule, and modified forms thereof.

In some embodiments, the ratio of nucleic acid origami structure to capsid protein mixed to produce the particles of the invention, by molarity, is at least 1:100, 1:200, 1:300, 1:400, 1:500, 1:600, 1:700, 1:750, 1:800, 1:900, 1:1000 or 1:2000. Each possibility represents a separate embodiment of the invention. In some embodiments, the ratio of nucleic acid origami structure to capsid protein, by molarity, is at least 1:200. In some embodiments, the ratio of origami structure to capsid protein, by molarity, is between 1:100 and 1:5000, 1:100 and 1:2000, 1:100 and 1:1000, 1:100 and 1:750, 1:200 and 1:5000, 1:200 and 1:2000, 1:200 and 1:1000, or 1:200 and 1:750. Each possibility represents a separate embodiment of the invention. In some embodiments, the ratio of origami structure to capsid protein, mixed to produce the particles of the invention, by molarity, is between 1:200 and 1:2000.

In some embodiments, the ratio of origami structure to capsid units in the particle is at least 1:12, 1:32, 1:42, 1:72, 1:92, 1:122, 1:132, 1:162, 1:212, 1:252, 1:272, 1:282, or 1:312. Each possibility represents a separate embodiment of the invention. In some embodiments, the ratio of nucleic acid origami structure to capsid structural units in the particle, by molarity, is at least 1:12, 1:32, 1:42, 1:72, 1:92, 1:122, 1:132, 1:162, 1:212, 1:252, 1:272, 1:282, or 1:312. Each possibility represents a separate embodiment of the invention.

In some embodiments, the particle comprising at least one origami structure encapsulated by the capsid units is a virus-like particle (VLP). In some embodiments, a VLP is capable of successfully transferring the encapsulated nucleic acid to a target cell, such that the nucleic acid may be expressed in the target cell. In some embodiments, a VLP is capable of transferring the encapsulated nucleic acid origami structure to a target cell, such that the nucleic acid may be expressed in the target cell, optionally after is has been unfolded in the cell, to allow expression. In some embodiments, the cell is in vitro. In some embodiments, the cell is harbored in a tissue, or an organism. In some embodiments, a VLP is capable of transferring the encapsulated nucleic acid origami structure in vivo to an organism, such that the nucleic acid may be expressed in vivo in a target cell or tissue. In some embodiments, the VLP is non-pathogenic. In some embodiments, the nucleic acid encapsulated in the particle is not of viral origin.

In some embodiments, the diameter of the particle is between 20 and 500, 20 and 400, 20 and 300, 20 and 250, 20 and 200, 20 and 150, 20 and 100, 30 and 500, 30 and 400, 30 and 300, 30 and 250, 30 and 200, 30 and 150, 30 and 100, 40 and 500, 40 and 400, 40 and 300, 40 and 250, 40 and 200, 40 and 150, 40 and 100, 50 and 500, 50 and 400, 50 and 300, 50 and 250, 50 and 200, 50 and 150, or 50 and 100 nm. Each possibility represents a separate embodiment of the invention. In some embodiments, the diameter of the particle is between 20 and 300 nm. In some embodiments, the diameter of the particle is greater than 20, 25, 30, 35, 40, 45, 50, 55, 60, or 65 nm. Each possibility represents a separate embodiment of the invention. In some embodiments, the diameter of the particle is the diameter of the virus-like particle.

In some embodiments, the particle of the invention allows for the encapsulation of nucleic acid molecules longer than can be encapsulated when the molecule is less compact. In some embodiments, the particle of the invention is more stable than a particle produced from a less compact nucleic acid molecule template. In some embodiments, the particle disclosed herein forms particle populations more uniform in size and shape than particle populations produced from a less compact nucleic acid molecule template.

In some embodiments, there are provided particles comprising at least one origami structure encapsulated by at least twelve capsid units.

In some embodiments, the particle of the invention has a different triangulation number (icosahedral geometry) than a particle produced from a less compact nucleic acid molecule template. In some embodiments, the particle of the invention has an icosahedral geometry more similar to naturally occurring virus than does a particle produced from a less compact nucleic acid molecule template. In some embodiments, the particle of the invention has a T=1, T=3, T=4, T=7, T=9, T=12, T=13, T=16, T=21, T=25, T=27, T=28, or T=31 icosahedral geometry. Each possibility represents a separate embodiment of the invention.

In some exemplary embodiments, the particle of the invention has a T=7 geometry. In some embodiments, the particle of the invention exhibit T=7d icosahedral symmetry. In some exemplary embodiments, the T=7d icosahedral particle capsid is composed of 12 pentavalent pentamers (for example, a VP1 pentamer that is surrounded by 5 other pentamers) and 60 hexavalent pentamers (for example, a VP1 pentamer that is surrounded by 6 other pentamers).

In some embodiments, an icosahedral surface lattice of the assembled capsid may include five-, three- and two-fold symmetry axes.

In some embodiments, the DNA origami structure is not randomly positioned with respect to the capsid geometry. In some embodiments, the interior (core) of the particle is uniform from particle to particle, i,e the population of particles, is substantially homogenous. In some embodiments, the DNA origami structure is randomly positioned with respect to the capsid geometry.

In some embodiments, the encapsulation efficiency of the DNA origami structure within capsid shell is over about 1%, over about 2%, over about 3%, over about 5%, over about 10%, over about 15%, over about 20%, over about 25%, over about 30%, over about 35%, over about 40%, over about 45%, over about 50%, over about 55%, over about 60%, over about 65%, over about 70%, over about 75%, over about 80%, over about 85%, over about 90%, over about 95%, or over about 99%. Each possibility is a separate embodiment.

In some embodiments, the encapsulation efficiency of DNA origami structure within the capsid shell is at least about 1%, at least about 2%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. Each possibility is a separate embodiment.

In some embodiments, there is provided a method for delivering/infecting/transfecting a target cell with the nucleic acid encapsulated in the particles of invention. In some embodiments, the particles of the invention are for use in delivering/infecting/transfecting a target cell with the nucleic acid encapsulated in the particles. In some embodiments, the particles of the invention are for use in delivering a nucleic acid molecule to a cell. In some embodiments, the particles of the invention are for use in delivering a nucleic acid molecule into a cell. In some embodiments, the particles of the invention are for use in delivering a nucleic acid molecule into the cytoplasm of a cell. In some embodiments, the particles of the invention are for use in delivering a nucleic acid molecule into the nucleus of a cell. In some embodiments, the particles of the invention are better at delivering a nucleic acid molecule into a cell as compared to VLPs (virus-like particles) containing less-compact nucleic acid molecules. In some embodiments, the particles of the invention are better at delivering a nucleic acid molecule into a cell as compared to conventional viral vectors. The terms "better delivery" and "better at delivering" are used interchangeably and can refer to any advantageous delivery, including, for example, but not limited to: ease of delivery, accuracy of delivery, efficiency and ease of production of particles, efficiency of expression of the nucleic acid in the target cell, efficiency of correction or inactivation of a target gene in the cell, an increased amount in the nucleic acid molecule entering the cell nucleus, an increased amount in the nucleic acid molecule entering the cell cytoplasm, the ability to deliver larger nucleic acid molecules to the cell, the ability to deliver multiple nucleic acid molecules to the same cell, the ability to deliver any type of nucleic acid molecules to the cell irrespective of their sequence, the ability to deliver multiple types of nucleic acid molecules to the same cell, the ability to deliver modified nucleic acid molecules to the same cell, the ability to deliver nucleic acids which are not of viral origin and increased protein production from the nucleic acid molecule in the cell, and the like. In some embodiments, advantageous delivery refers to the lack on immunogenicity of the particles of the invention. In some embodiments, the particles of the invention are for use in delivering/infecting/transfecting of the nucleic acid molecules to a desired target site. The target site may include any target site, such as, but not limited to: a cell, a tissue, an organ, a microorganism, and the like. The target site may be an in vivo or in vitro target site.

In some embodiments, the cell is in vitro. In some embodiments, the cell is in vivo. In some embodiments, the cell is in vitro or in vivo. In some embodiments, the cell is a human cell. In some embodiments, the cell is a mammalian cell.

In some embodiments, there is provided a composition comprising one or more particles of the invention. In some embodiments, the composition includes a plurality of the particles of the invention. In some embodiments, the composition is a pharmaceutical composition, comprising a pharmaceutically acceptable carrier. In some embodiments, the composition may include a plurality of particles that may be identical or different with respect of the size, composition and/or identity of the nucleic acid encapsulated in the particle and/or the capsid units of the particles.

In the application, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

The following examples serve to illustrate certain embodiments and aspects of the present invention and are not to be construed as limiting the scope thereof. Those skilled in the art will appreciate that many changes could be made in the specific embodiments disclosed herein while still obtaining an identical or similar result.

Materials and Methods

Particle Production (Production of Virus-Like Particle (VLP))

The self-assembly of particles in vitro requires the use of the purified capsid protein and a nucleic acid origami structure. In the examples below, empty VP1-VLPs were produced as a source of VP1 pentamers for assembly. SV40 VP1 was produced in SF9 cells infected by a Baculovirus expression vector (VP1 UniProt entry—P03087).

The empty VLPs formed inside the SF9 cells were extracted by performing cellular lysis and purified on a CsCl gradient. VLPs were disassembled in vitro into basic VP1 pentameric capsid units. Pentamers were obtained by dissociating VLPs by dialysis first against 20 mM Tris-Cl, pH 8.9, 50 mM NaCl 2 mM DTT (dissociation buffer) with 5 mM EDTA and then against dissociation buffer with 2 mM EDTA at 4° C. All dialysis steps were carried out in presence of complete protease inhibitor (Roche). The dialysate was centrifuge at 20,000 g for 30 min at 4° C. to sediment aggregated protein.

For assembly of the particles, the nucleic acid origami structure was added to disassembled VP1 pentamers in 2× assembly buffer (250 mM NaCl, 100 mM MOPS pH 7.2). The capsid was assembled spontaneously around the nucleic acid. For assembly reactions, the nucleic acid templates were: 2873-nt long single stranded DNA structured into 25 nm near-spherical origami structure, 5386-nt long ΦX174 Virion DNA structured into 30 nm near-spherical origami structure, 7560-nt long single stranded DNA, based on a M13mp18 bacteriophage derivative, structured into 35 nm near-spherical DNA origami structure and 40 nm near-spherical origami structure composed of two half spheres: the first is based on a 7249 nucleotide-long scaffold DNA strand based on a M13mp18 bacteriophage derivative, and the second is based on a 7560 nucleotide-long scaffold DNA strand based on a M13mp18 bacteriophage (All origami structures are commercially available from tilibit nanosystems, Garching, Germany).

Origami Structure

As detailed above, origami structures were purchased from tilibit nanosystems, Garching, Germany. Likewise, fluorescently labeled 30 nm near-sphere DNA origami, composed of 5386-nt ΦX174 Virion DNA with 25 Cy5 modified staples was purchased.

Negative Stain Transmission Electron Microscopy (TEM)

A 3 µl drop of the sample was applied to a glow discharged grid (carbon support film on 300 mesh Cu grids, Ted Pella, Ltd.). After 10-20 seconds(s) the excess liquid was blotted with a filter paper. The grids were incubated with 2% Uranyl acetate stain for 30 s, blotted and allowed to dry in air. The samples were studied by a FEI Tecnai 12 G² TWIN TEM operated at 120 kV and the images were recorded by a 4K×4K FEI Eagle CCD camera.

Cryo-EM

Sample Preparation

For single particle analysis 3 µl VLP samples were applied to holey carbon grids (Quantifoil R 1.2/1.3, Micro Tools GmbH, Germany) after 30 seconds glow discharge treatment. Grids were blotted and vitrified by rapidly plunging into liquid ethane at −182° C. with a Vitrobot (FEI, Eindhoven).

Data Acquisition for Single Particle Analysis:

Samples were imaged under low-dose conditions on a FEI Tecnai F30 Polara microscope (FEI, Eindhoven) operating at 300 kV. Datasets were automatically collected using SerialEM on a K2 Summit direct electron detector camera fitted behind an energy filter (Gatan Quantum GIF) with a calibrated pixel size of 2.3 Å. The energy filter was set to remove electrons >±10 eV from the zero-loss peak energy. The K2 summit camera was operated in counting mode at a dose rate of 10 electrons/pixel/second on the camera. Each movie was dose fractionated into 50 image frames, with total electron dose of 80 $\bar{e}/Å^2$.

Single Particle Reconstruction

Dose-fractionated image stacks were aligned using MotionCorr2, and their defocus values estimated by Gctf. The sum of the aligned frames was used for further processing and the rest of the processing was done in RELION2.1. 48778 particles were autopicked and subjected to 2D classification using RELION 2.1 with 100 classes. The initial 3D reference was prepared from 3200 empty capsid particles of distinct selected 2D class averages. We performed 3D classification and refinement of the empty capsids from 26,110 pariceles imposing icosahedral symmetry (11). The resulting empty capsid map was then used as an initial reference model for 3D classification and refinement of the origami-filled capsids (19786 particles). Reconstruction of a 3D cryo-EM map of the origami-filled capsid was confirmed using de-novo 3D initial model generated in RELION 3.0.

Correct handedness of the empty capsid was assessed by the quality of fit to the SV40 crystal structure (PDB ID 1SVA), by measuring correlation coefficients using the UCSF Chimera protocol "Fit in Map"; the correlation coefficients was 0.952 (as opposed to 0.907 for the opposite hand).

Confocal Microscopy Assay

VLPs were prepared by using the following capsid protein pentamer/DNA molar ratios: 200, 400, 750 (fluorescently labeled 30 nm DNA origami structure—3.75 nM, 1.9 nM, 0.95 nM; VP1 pentamers-750 nM). 25 µL of VLPs was then mixed with 300 µL of serum-free medium and overlaid on CV1 cells in 24 multi-well plates for 1 hour. Then, 1 ml of serum-containing medium was added to the wells. Intracellular uptake of fluorescent DNA was visualized 24 hours later by confocal microscopy.

Example 1: Assembly of SV40 VP1 on DNA Origami

Origami structure DNA in the form of near-spheres, were used for the particle preparation. Origami DNA structures of the indicated diameters were purchased from tilibit nanosystems, Garching, Germany: 25 nm, 30 nm, 35 nm and 40 nm (shown in the Electron micrographs of FIGS. 1A-D). Additionally, a 30 nm DNA origami structure with 25 staples modified with a Cy5 fluorescent tag was used. All DNA origami structures were incorporated into the particles (VLPs) and used in the herein described experiments.

Capsid units made of pentamers of SV40 capsid protein VP1 were used for encapsulation of the origami structures. For negative staining TEM, cryo-EM and agarose gel analysis, VLPs were prepared by using 400:1 pentamers/origami structure ratio: (pentamers—4 µM; origami structures—10 nm).

Example 2: Formation of Virus-Like Particles

Figure 2A:
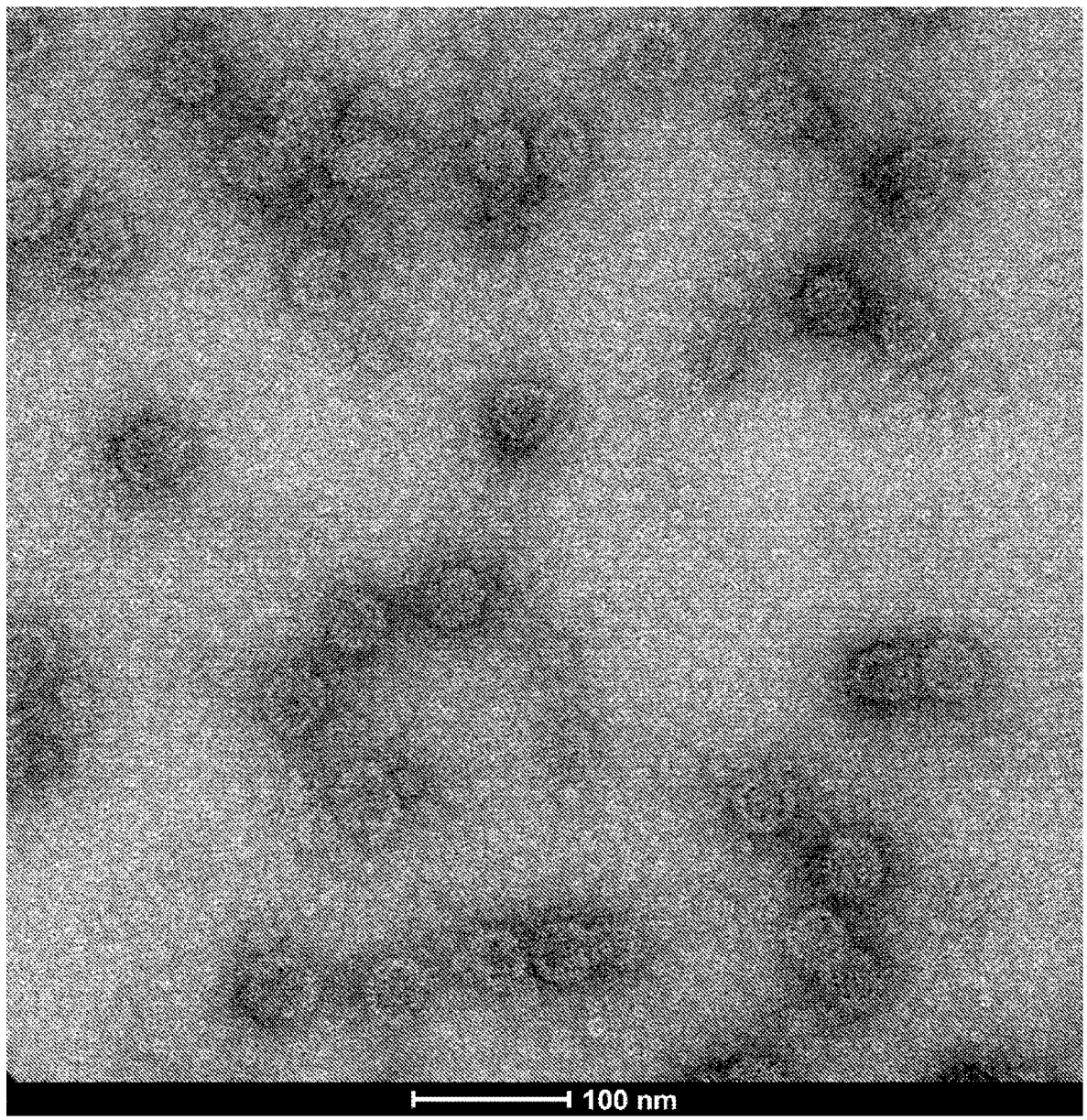
FIGS. 2A-D: Negative staining Transmission Electron Microscopy of particles.
Figure 2B:
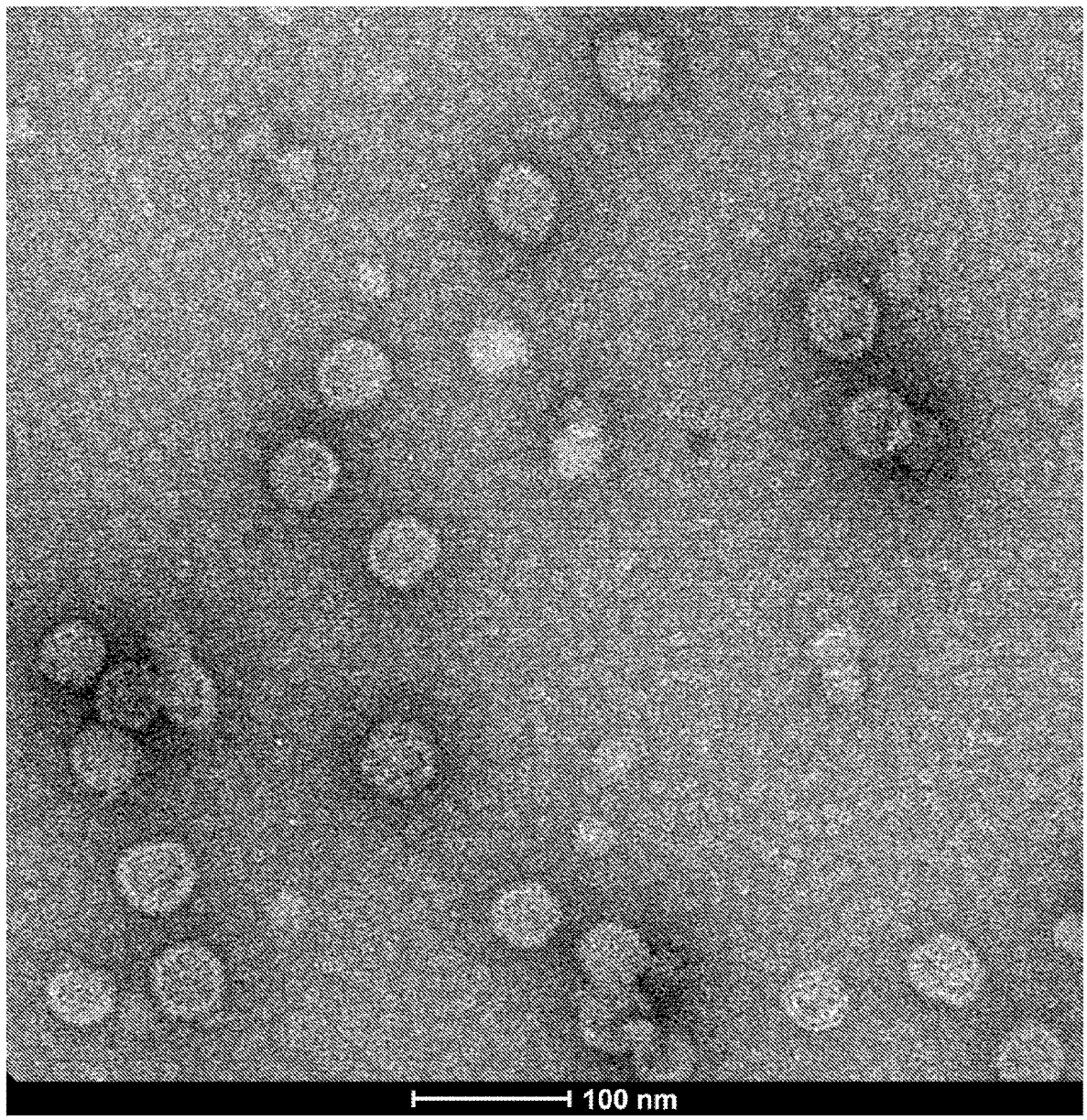

Negative staining Transmission Electron Microscopy (TEM) was used to confirm the formation of VLPs. VLPs were negatively stained with 2% uranyl acetate and imaged. Assembly of VP1 on 25 nm DNA origami structure leads to formation of 36-38 nm particles (as shown in FIG. 2A). Assembly of VP1 around DNA origami structure of 30 nm diameter leads to formation of 50 nm particles (as shown in FIG. 2B).

Figure 2C:
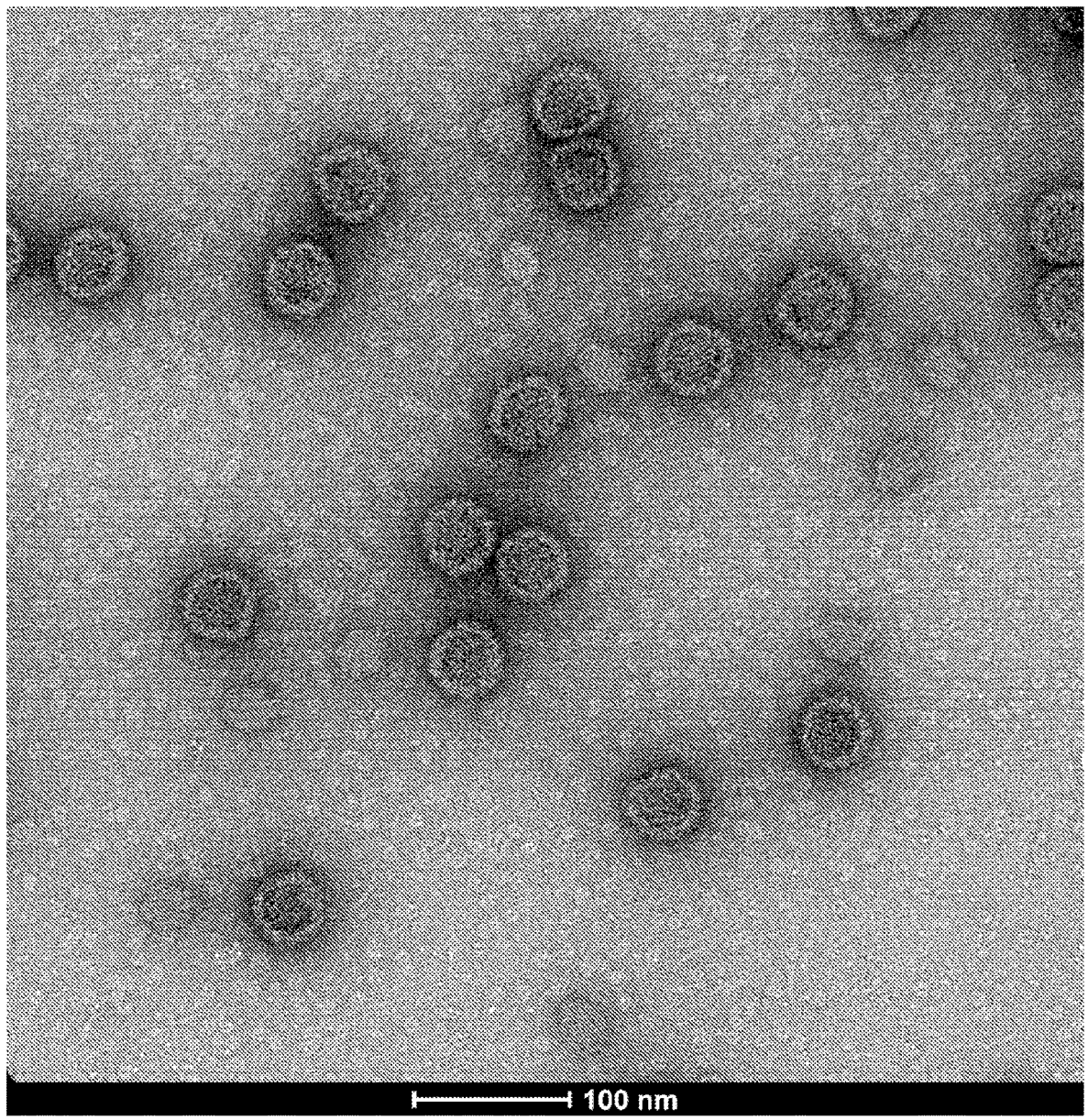

Assembly of VP1 around near-spherical DNA origami structure of 35 nm diameter leads to formation of 50 nm particle as well (As shown in FIG. 2C).

Figure 2D:
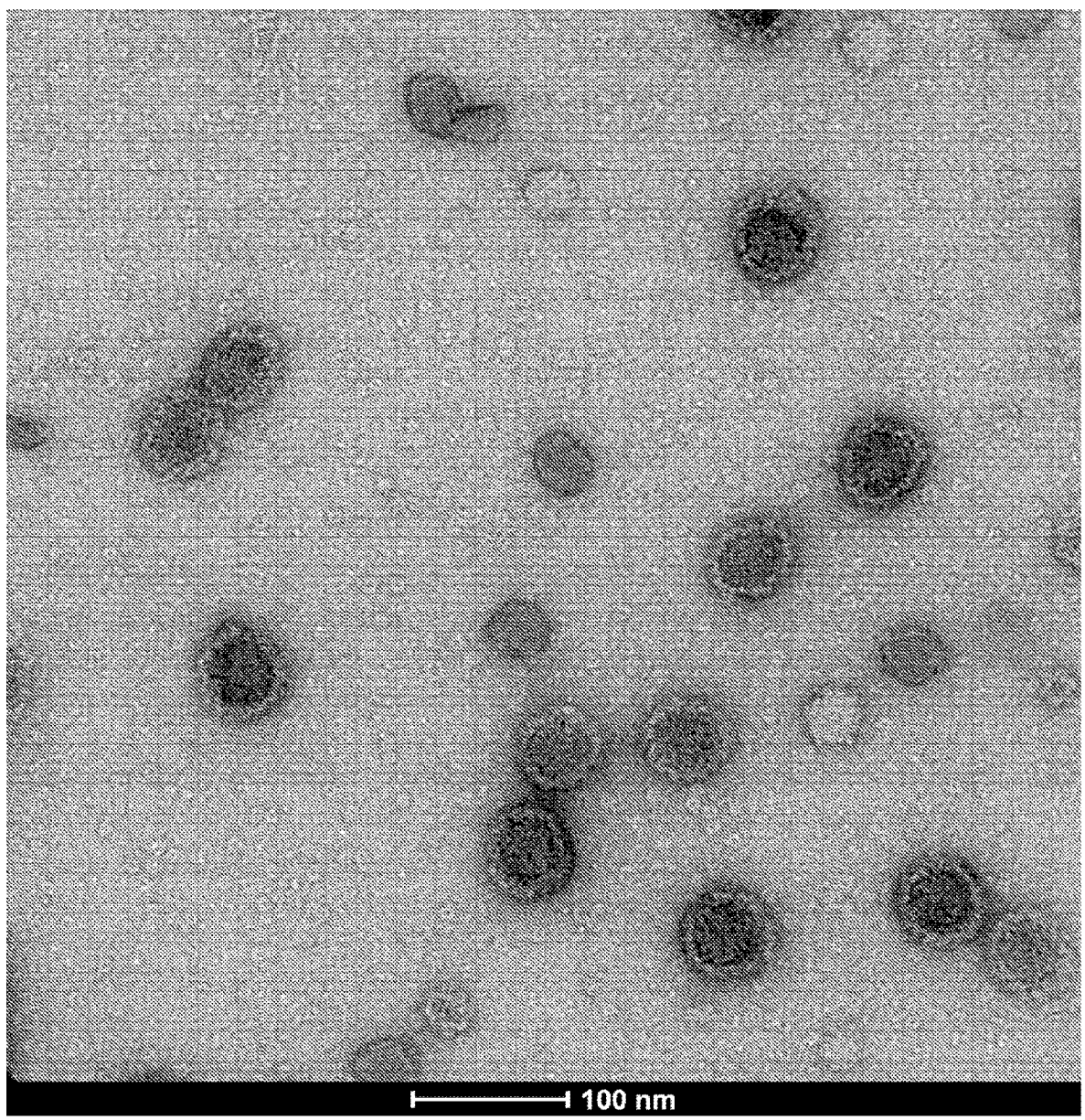

Assembly of VP1 around near-spherical DNA origami structure of 40 nm in diameter leads to formation of 56 nm particle. (As shown in FIG. 2D).

The particles obtained by assembly of VP1 around 25 nm and 40 nm DNA origami structures represent entirely new forms of SV40 particles, with non-native capsid sizes, suggesting geometry of T=3 or 4 and T=12, respectively. These results suggest that T, the triangulation number characteristic of icosahedral capsid geometry, may adjust to accommodate the size of origami structures. Thus, the results demonstrate that there is much flexibility in accommodating different DNA origami sizes, suggesting flexibility in the bond angles between adjacent pentamers.

Figure 3A:
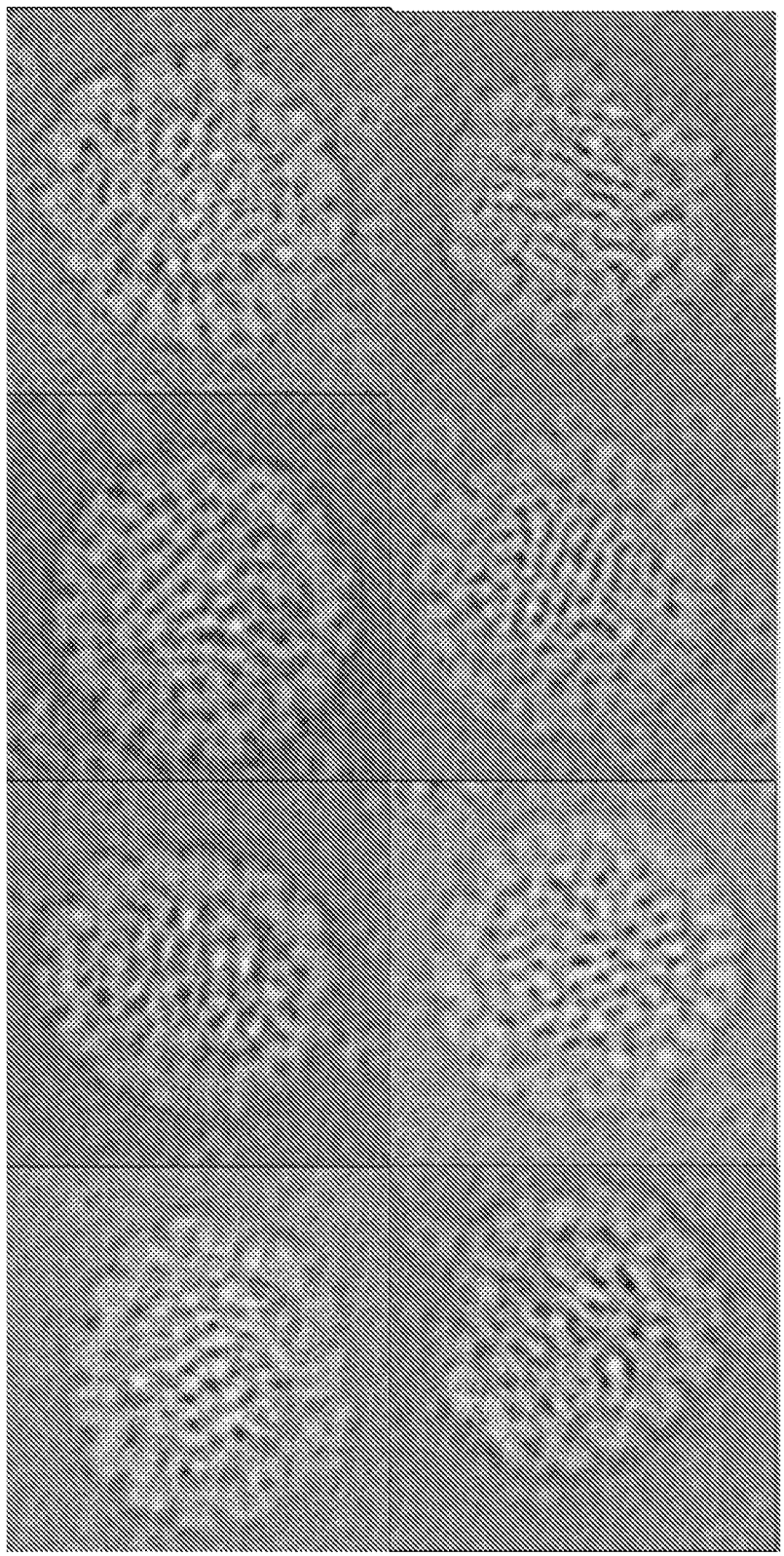
FIG. 3A: Eight cryo-EM 2D micrographs of particles built of SV40 VP1 assembled on 30 nm nearly spherical DNA origami structure. The micrographs show 50 nm SV40-like particles, comprised of a shell exhibiting characteristic viral spikes (VP1 pentamers) and a core. In some of the cores the folded strands of the origami structure can be observed (seen as stripes).
Figure 3B:
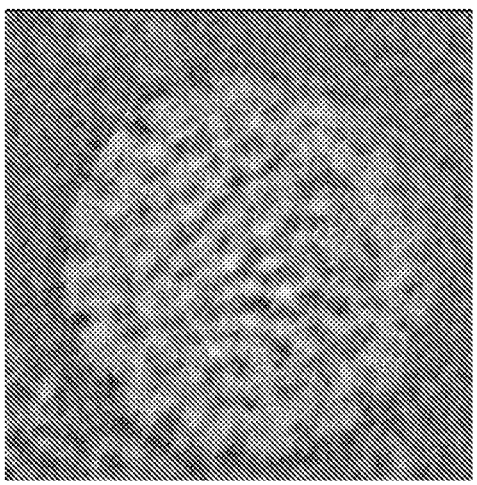
FIG. 3B: model of wild type SV40 (PDB entry 1SVA) superimposed on 2D micrograph of SV40-like particle assembled on 30 nm nearly spherical DNA origami structure, showing perfect alignment.
Figure 3B:
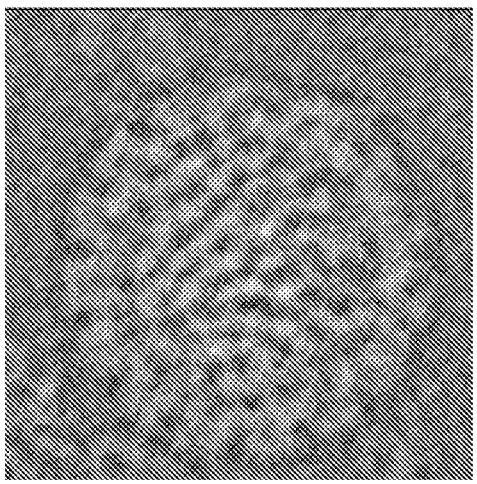
Figure 3B:
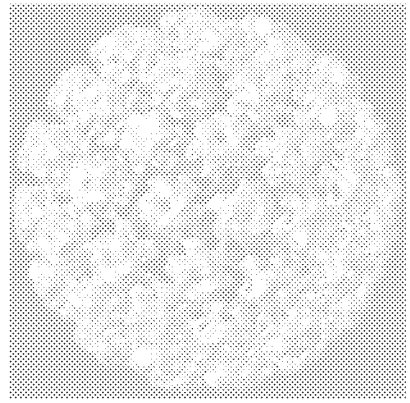
Figure 3C:
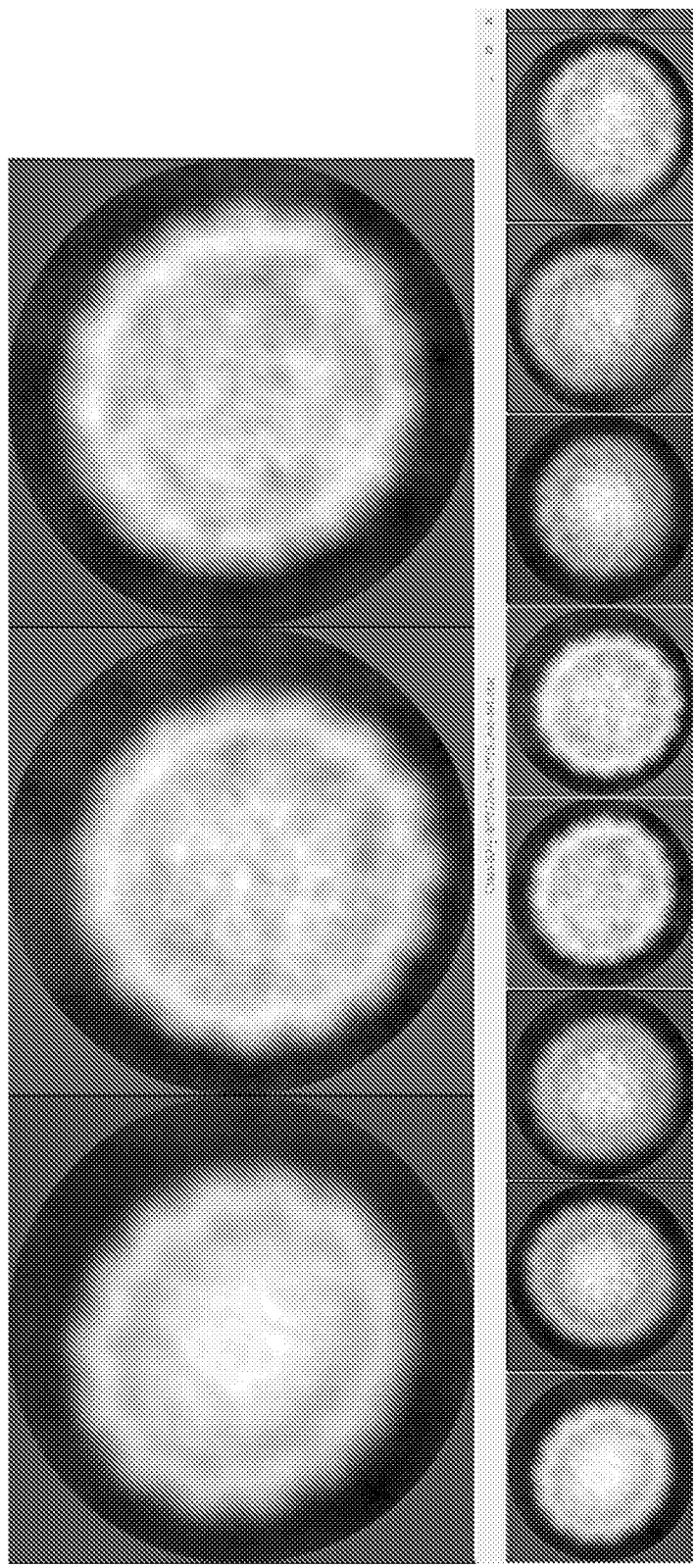
FIG. 3C: 2D classification of Cryo-EM micrographs that sorts particles assembled on 30 nm nearly spherical DNA origami structure into classes of similar particles, each subclass representing an average of several hundred particles.

Example 3: Cryo-EM of SV40-Like Particles Assembled on 30 nm Nearly-Spherical DNA Origami Structure Cryo-EM 2D micrographs of eight typical particles formed by VP1 assembly on 30 nm near-spherical DNA origami were performed. The resulting particles are practically identical to SV40 in terms of size and shape. Particles are comprised of a shell exhibiting characteristic viral spikes on the circumference (VP1 pentamers) and a core. In some of the cores, the folded strands of the origami structure are visible (seen as stripes), as shown in FIG. 3A. To demonstrate resemblance to native virus, the 3D model of wild type SV40 (PDB entry 1SVA) shows perfect alignment when superimposed on the synthetic particle (FIG. 3B). 2D classification of Cryo-EM micrographs sorts particles into classes of similar particles, each subclass representing an average of several hundred particles. Subtypes are all very similar to each other and exhibiting viral characteristics, as illustrated in FIG. 3C. The 2D class averaging results in a disordered 'cloud' of density in the core of the particle, suggesting that DNA origami structure is randomly oriented with respect to capsid geometry. This suggests that the 30 nm DNA origami structure is smaller than SV40 capsid cavity, which leaves some degree of freedom of the origami structure in the capsid (as can also be seen when comparing below to class averages of particles encapsulating the larger, 35 nm origami structure, in which the structural details of DNA origami are clearly observed, as well as to FIG. 7).

Example 4: Delivery of Nucleic Acid Origami into Cells

Figure 4A:
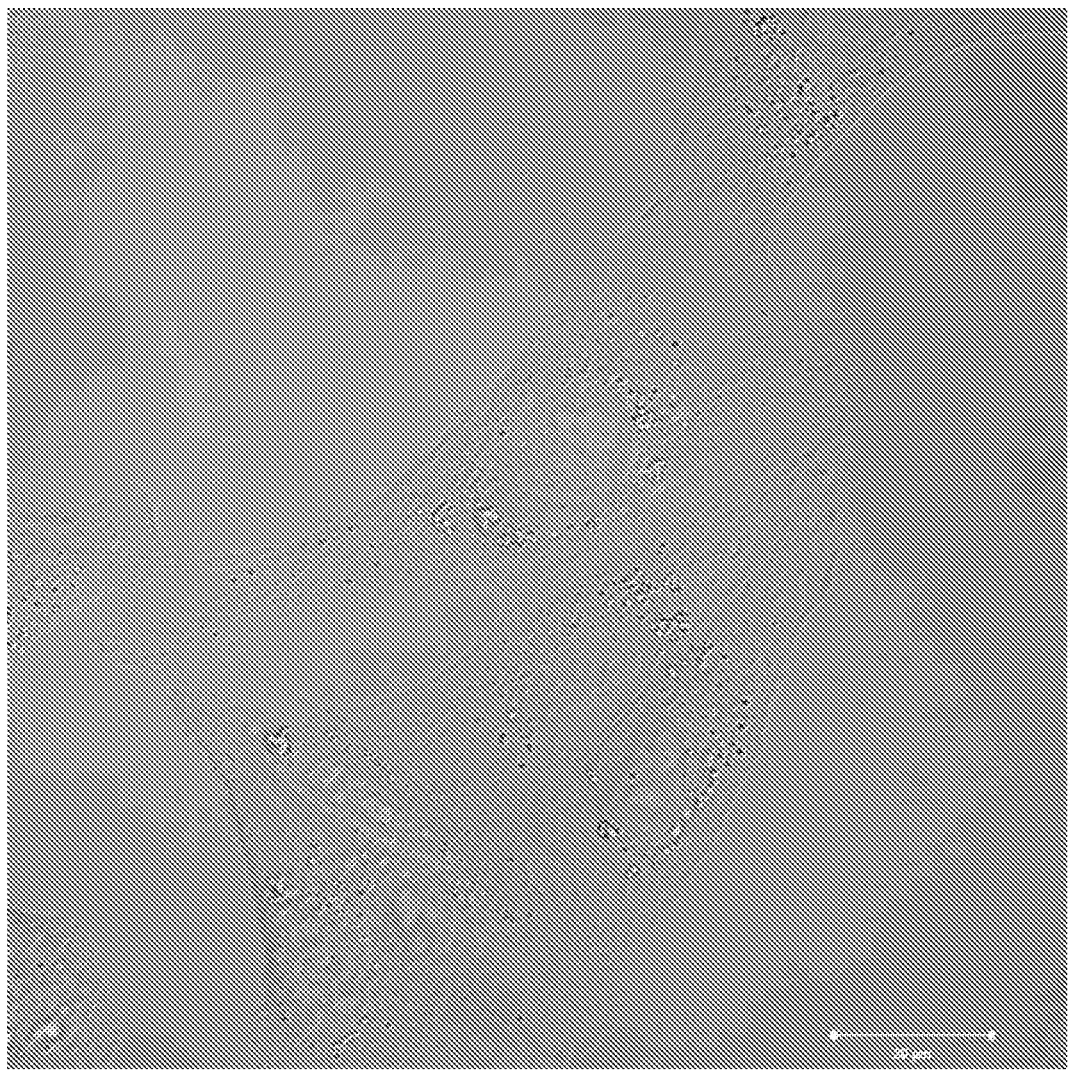
FIGS. 4A-B: Confocal micrographs of CV-1 cells incubated with fluorescently labeled naked 30 nm origami structure or with SV40-like particles containing labeled 30 nm DNA origami structure.
Figure 4B:
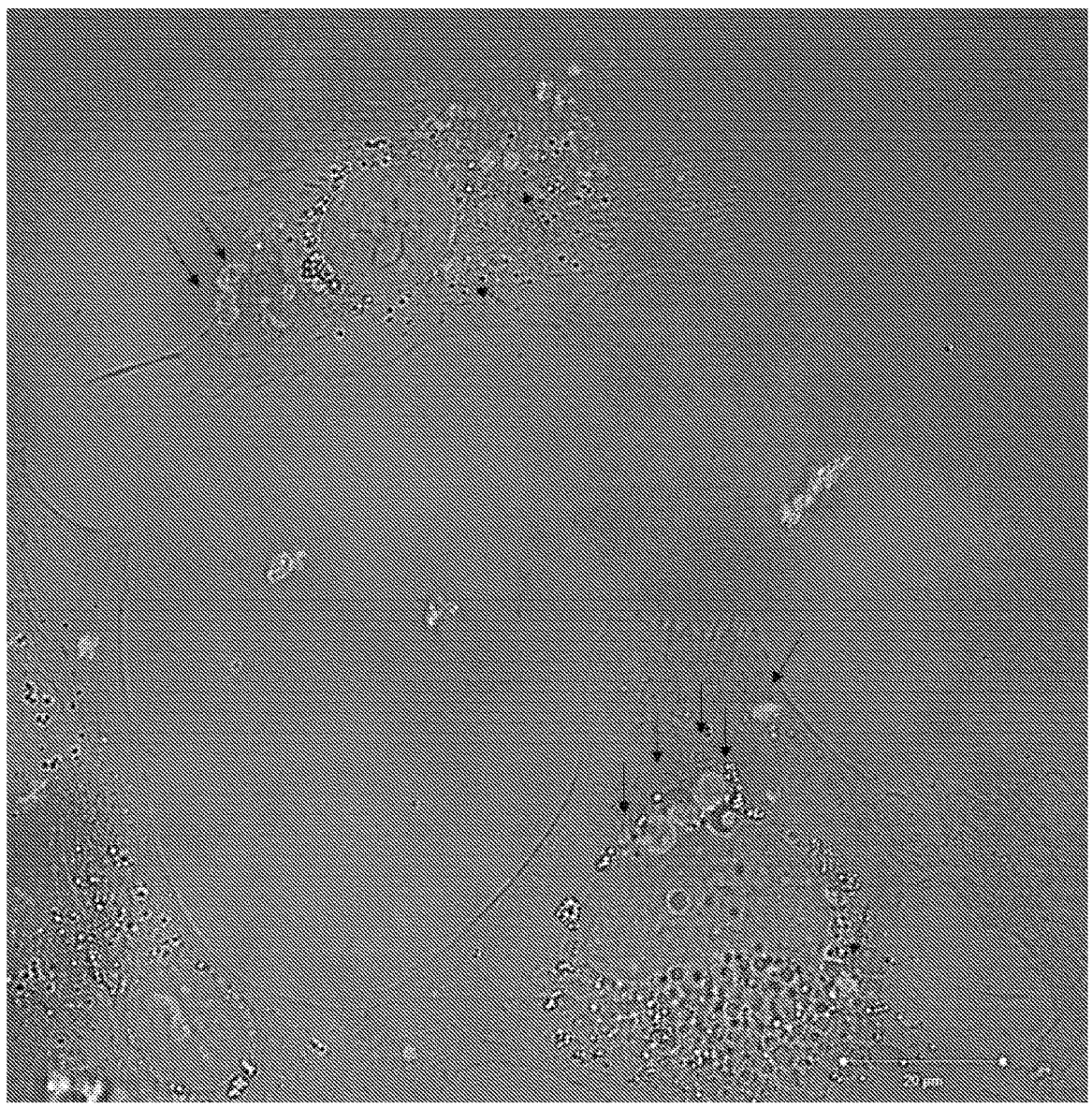

Fluorescent particles prepared with Cy5-tagged 30 nm origami DNA when added to CV1 cells exhibited significant infection rates. The results are presented in FIGS. 4A-B: Cells provided with naked origami DNA did not show any fluorescence after 24 hours (FIG. 4A). However, as seen at 24 hours after infection, fluorescent particles assembled on Cy5-tagged origami DNA are seen within the cells and indeed seem to accumulate at the Golgi, which is one of the destinations of the intracellular trafficking pathway of wild-type SV40. Fluorescent particles are marked by black arrows (FIG. 4B).

Thus, the results demonstrate effective recognition and intracellular internalization of DNA-encapsulated particles.

Figure 5A:
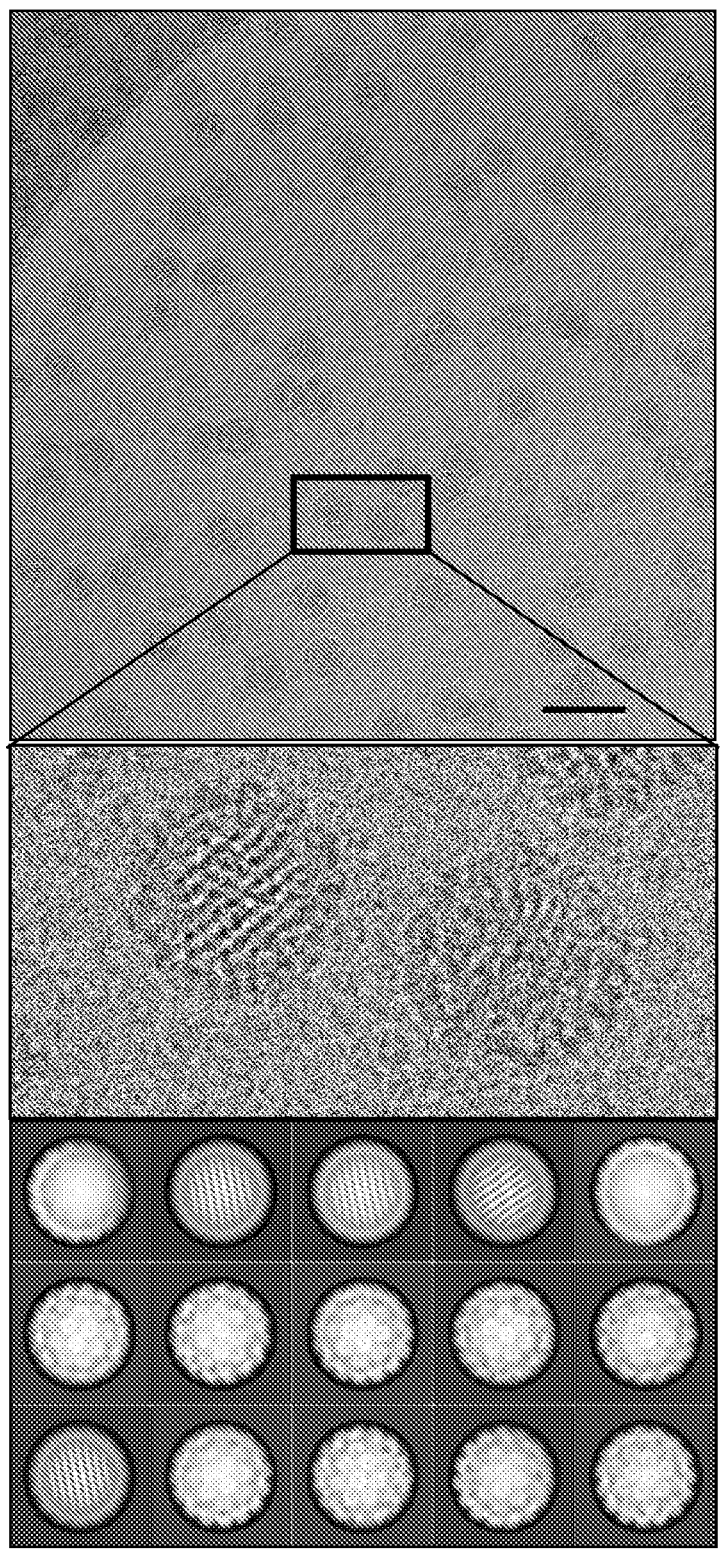
FIGS. 5A-5E: Cryo-EM and 3D reconstruction of a T=7d icosahedral SV40-like particles assembled on 35 nm nearly spherical DNA origami structure.

Example 5: Cryo-EM and 3D Reconstruction of a T=7d Icosahedral SV40-Like Particles Assembled on 35 nm Nearly-Spherical DNA Origami Structure Cryo-EM micrographs of SV40 VP1 assembled on 35 nm spherical DNA origami structure show the presence of 50-nm virus-like particles, which resembled wild type SV40 in size, spherical shape and the characteristic viral pentamers (FIG. 5A, top panel). The particles mixture clearly consisted of two populations of virus-like particles (VLPs): empty and origami-filled. Representative micrographs of empty and filled particles are shown enlarged (FIG. 5A, inset, middle panel), with DNA clearly distinguished in the core of the left particle as stripes, representing the folded strands of the origami structure. To reconstruct the 3D model of the particles a total of 48778 individual particles were auto-picked (RELION2.1) from 1666 micrographs. Particles were subjected to 2D classification that confirmed the presence of both empty and DNA filled capsid class averages. (FIG. 5A, bottom panel).

Figure 5B:
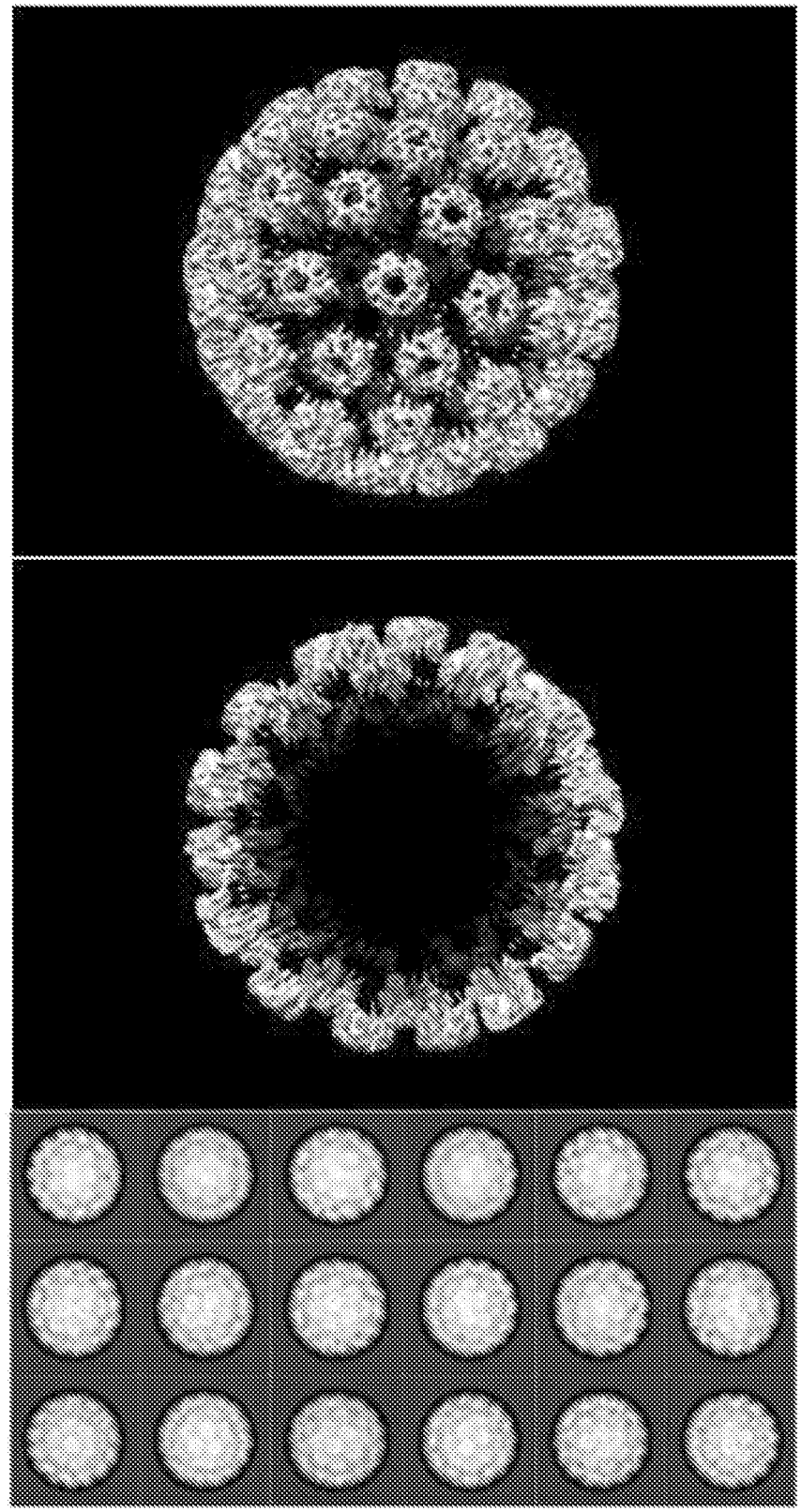

Reconstruction of a 3D model of empty particles was calculated from 26110 particles yielding T=7d icosahedral capsids at a resolution of 7.3 Å (FIG. 5B, see below for Caspar and Klug method of calculation of the icosahedral triangulation number).

Figure 5C:
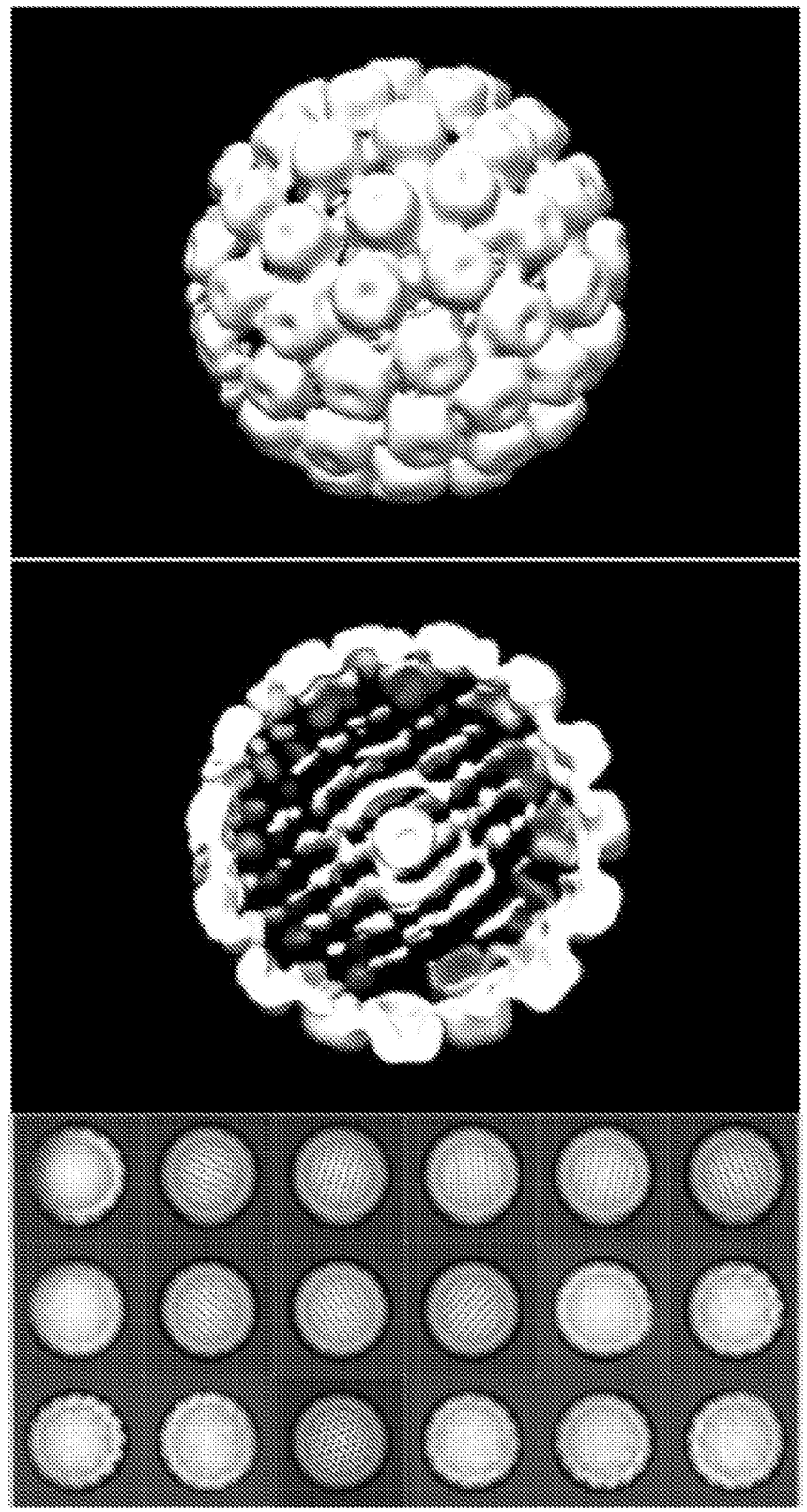

Due to the asymmetric nature of the DNA origami, 3D reconstruction of the origami filled particles was done without imposing icosahedral symmetry. 3D reconstruction of 19786 particles containing the asymmetric DNA origami was calculated using the empty capsid structure as an initial model, shown at ~25 Å resolution in FIG. 5C. The lower resolution of the structure, compared to that of an empty particle, is probably due to the lack of imposed symmetry. Despite the lack of any symmetry averaging, the protein shell of the reconstructed origami filled particle is clearly icosahedral (FIG. 5C top panel, see below for the calculation of icosahedral triangulation number). Inside the shell, the parallel helices of DNA origami lattice are clearly visible (FIG. 5C, middle panel). Reconstruction of a 3D model of the origami-filled capsid was confirmed using de-novo 3D initial model.

Figure 5D:
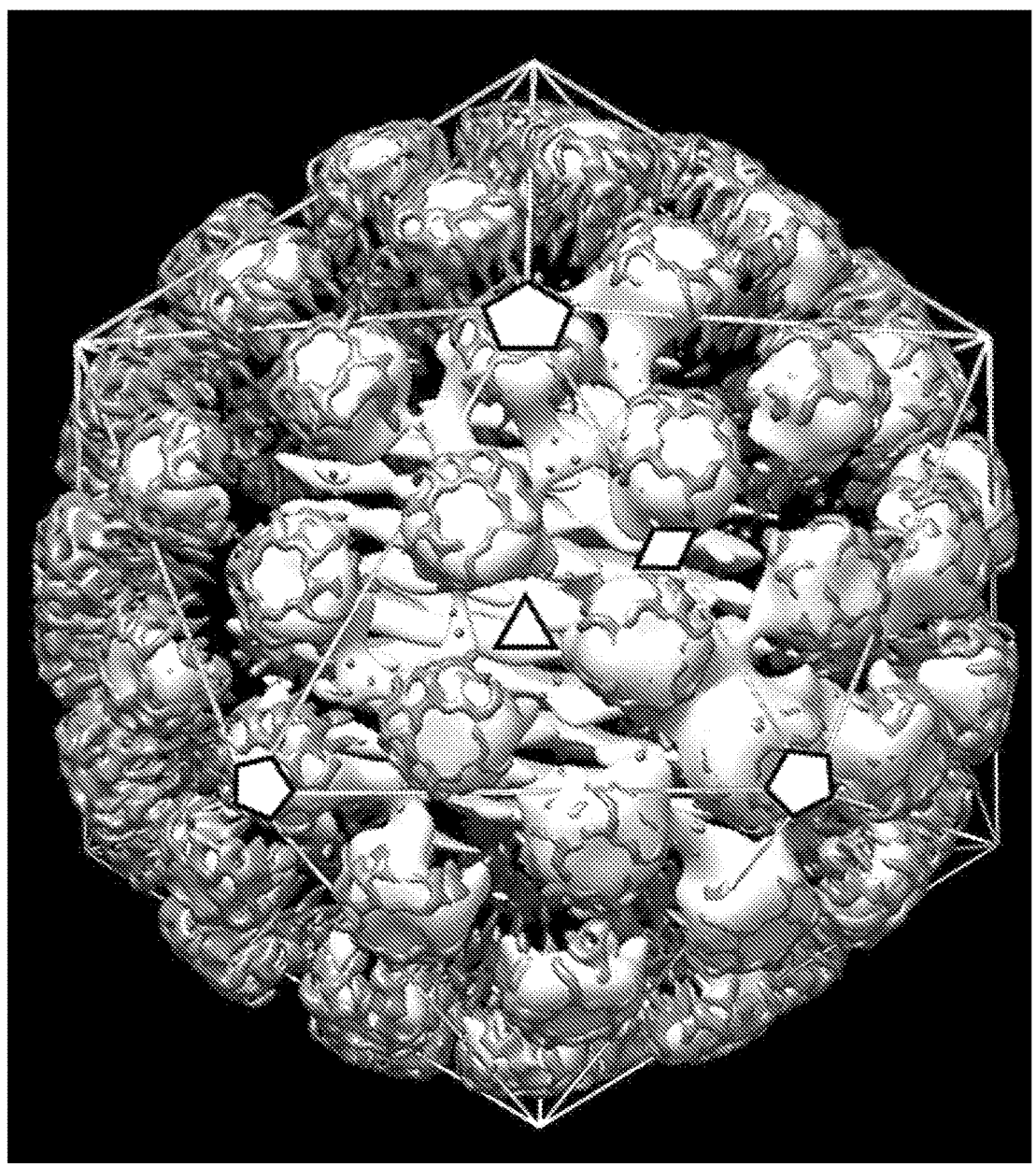

As shown, the particles clearly exhibit T=7d icosahedral symmetry according to Caspar and Klug theory of viral tiling (Physical principles in the construction of regular viruses. Cold Spring Harb Symp Quant Biol. 1962; 27:1-24)). First, icosahedral capsids possess 5-fold, 3-fold and 2-fold rotation axes (see FIG. 5D). To demonstrate the icosahedral symmetry, an icosahedron was manually fitted to the surface of the cryo-EM reconstructed origami-filled capsid by aligning its vertices to the center of the pentavalent pentamers in the shell. The five-, three- and two-fold symmetry axes are marked as pentagons, triangle and rhombus respectively.

Figure 5E:
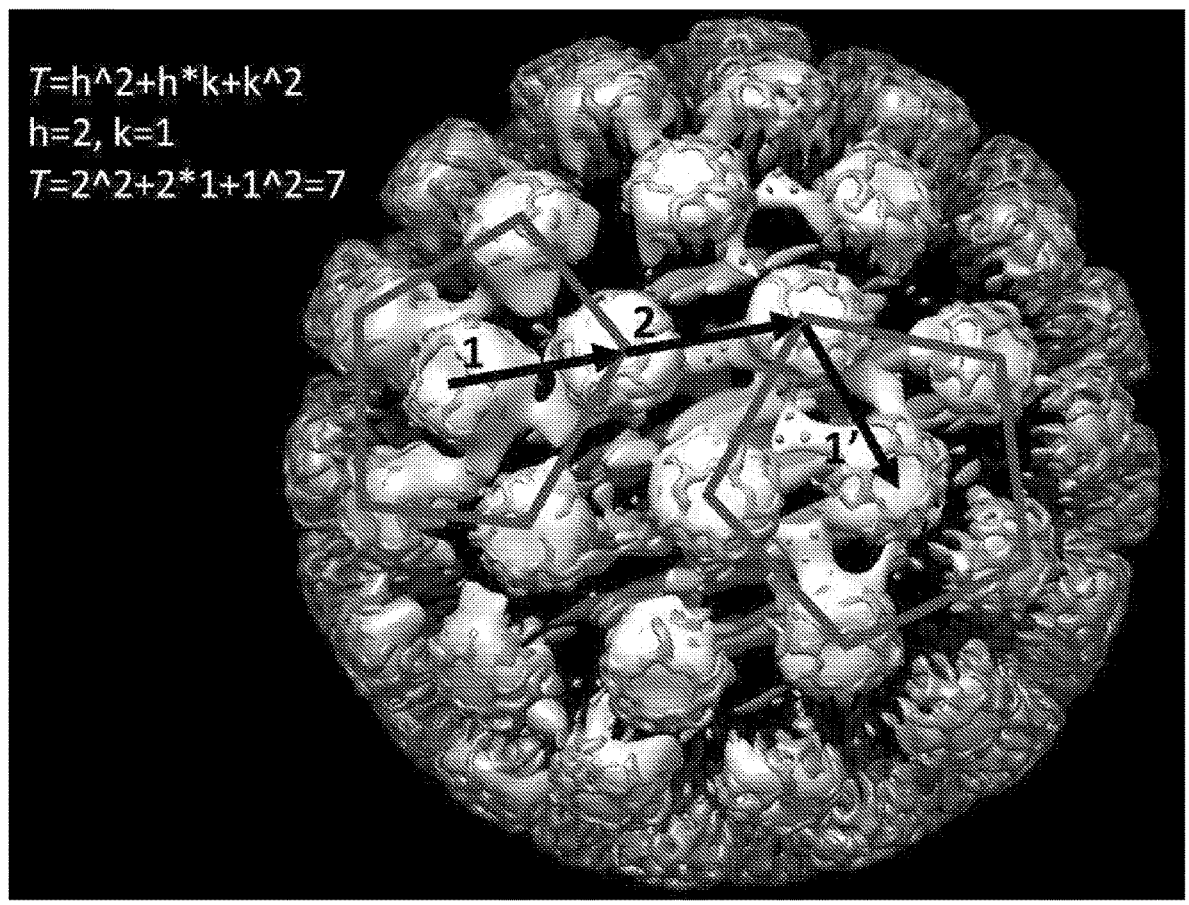

Second, SV40 T=7d icosahedral capsid is composed of 12 pentavalent pentamers (a VP1 pentamer that is surrounded by 5 other pentamers) and 60 hexavalent pentamers (a VP1 pentamer that is surrounded by 6 other pentamers). As shown in FIG. 5E, Pentavalent pentamers are indicated by pentagons. The black arrows illustrate the Caspar and Klug method of calculation of the icosahedral triangulation number (T). T is given by the rule: $T=h^{}2+hk+k^{}2$, for all pairs of integers, where h and k define the position of a pentavalent pentamer relative to the nearest positioned pentavalent pentamer on the icosahedral lattice. For T=7d, h=2 and k=1, h represented by arrows 1 and 2 while K represented by arrow 1'. The localization of pentavalent VP1 pentamers in the capsid assembled on DNA origami clearly corresponds to T=7d (see FIG. 5E for illustration).

Thus, altogether, the results clearly indicate that origami structure is encapsulated within the protein shell of the particles and the protein shell forms a regular SV40 lattice of T=7d icosahedral symmetry.

Figure 6A:
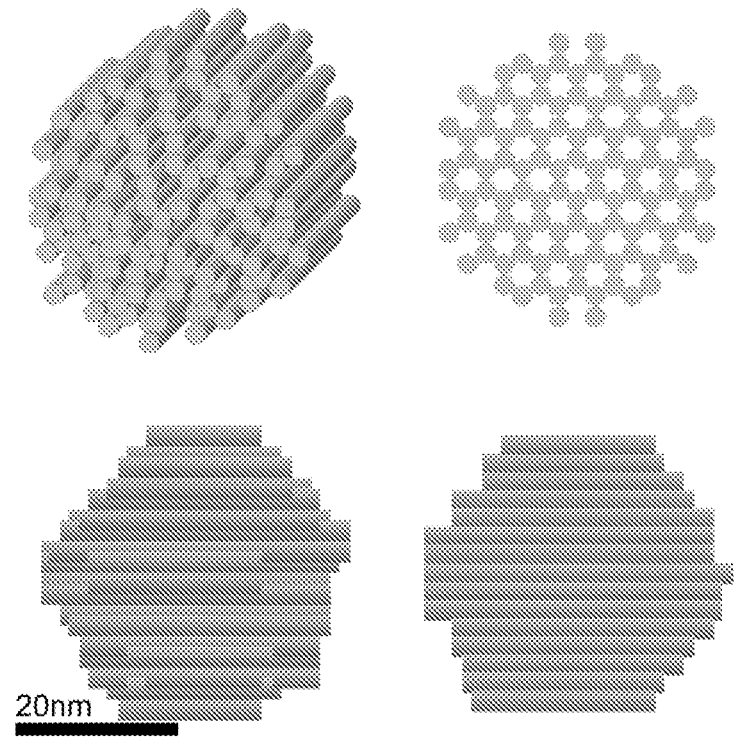
FIGS. 6A-B: Internal views of the cryo-EM 3D reconstruction of SV40-like particles assembled on DNA origami showing that DNA origami is encapsulated in its entirety.
Figure 6B:
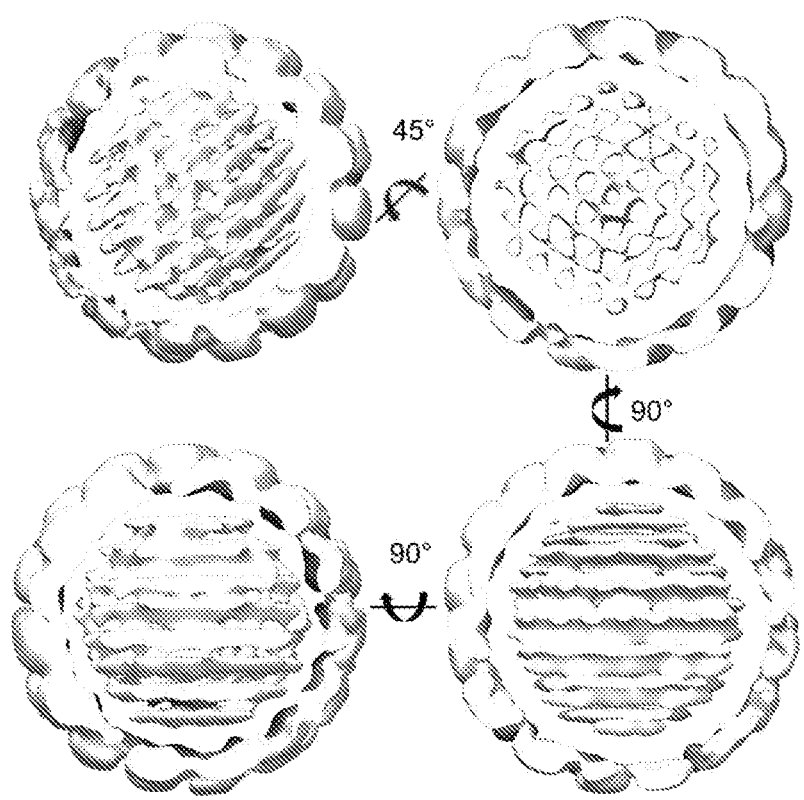

Example 6: Internal Views of Cryo-EM 3D Reconstruction of SV40-Like Particles Assembled on 35 nm DNA Origami, Showing that DNA Origami is Encapsulated in its Entirety A schematic representation of the 35 nm DNA origami structure is shown at different observation angles in FIG. 6A. The corresponding views of 3D electron density map of 3D reconstruction of DNA origami-filled capsid are shown side by side with the different views of the schematic design of DNA origami (FIG. 6B). The honeycomb lattice organization of DNA origami is clearly visible (FIG. 6B top right), as also 45-degree inward inclination of the honeycomb lattice (FIG. 6B top left) and as 90-degree rotations around axes that are perpendicular (FIG. 6B bottom right) and horizontal (FIG. 6B bottom left) to the longitudinal axis, connecting the two honeycomb planes. Each of the rotated views of the reconstructed particle exactly depicts the features predicted by the respective view of the DNA origami schematic design.

Thus, altogether, all structural features of origami structure, the parallel helices arranged in a "honeycomb" lattice, in all possible projections, are clearly visible inside the capsid, indicating that DNA origami is completely encapsulated within the protein shell of the particle. Further, the results shown in FIGS. 7A-C, demonstrate that the 35 nm DNA origami structure is not randomly positioned with respect to the capsid geometry, as apparent from the shown cut-away views, where the capsid was removed from the front, and the capsid lattice has been rotated so either the threefold (FIG. 7B), twofold (FIG. 7A) or fivefold (FIG. 7C) symmetry axis of the icosahedron is depicted. In each case it seems that the viewer is faced by a different facet of the DNA origami. For example, the honeycomb facet can be viewed along an axis slightly off (6.8°) the icosahedron threefold axis (FIGS. 7A and 7B).

Example 7: Detection of Capsid Proteins-Nucleic Acid Origami Structure Complexes Electrophoretic Mobility Shift Assay (EMSA) provides evidence for formation of protein-nucleic acid complexes and are used to observe pentamer-DNA origami interaction.

Figure 8:
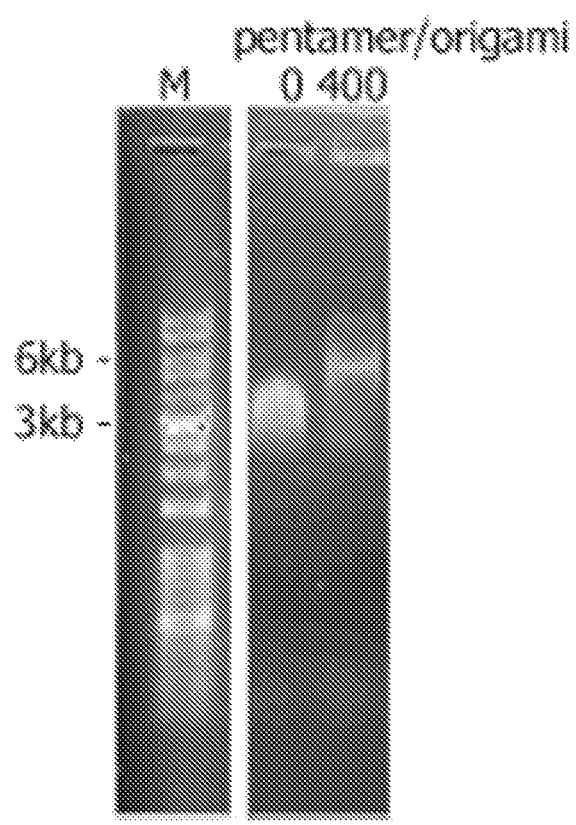

For the EMSA experiments, 35 nm DNA origami structure was mixed with VP1 pentamers at a molar ratio of 400 pentamers per DNA origami structure. Assembly products were analyzed on agarose gel to identify migration. The results are presented in FIG. 8. Free DNA origami migrated with the 4 kb ds DNA size marker. When incubated with VP1 proteins, the free DNA origami band disappeared and instead appeared a slower migrating, well-defined band. The appearance of a new well-defined band of higher molecular weight suggests the formation of a stable and well-defined VP1/DNA origami complex.

Example 8: Unfolding of DNA Origami Under Intracellular Conditions

Figure 9:
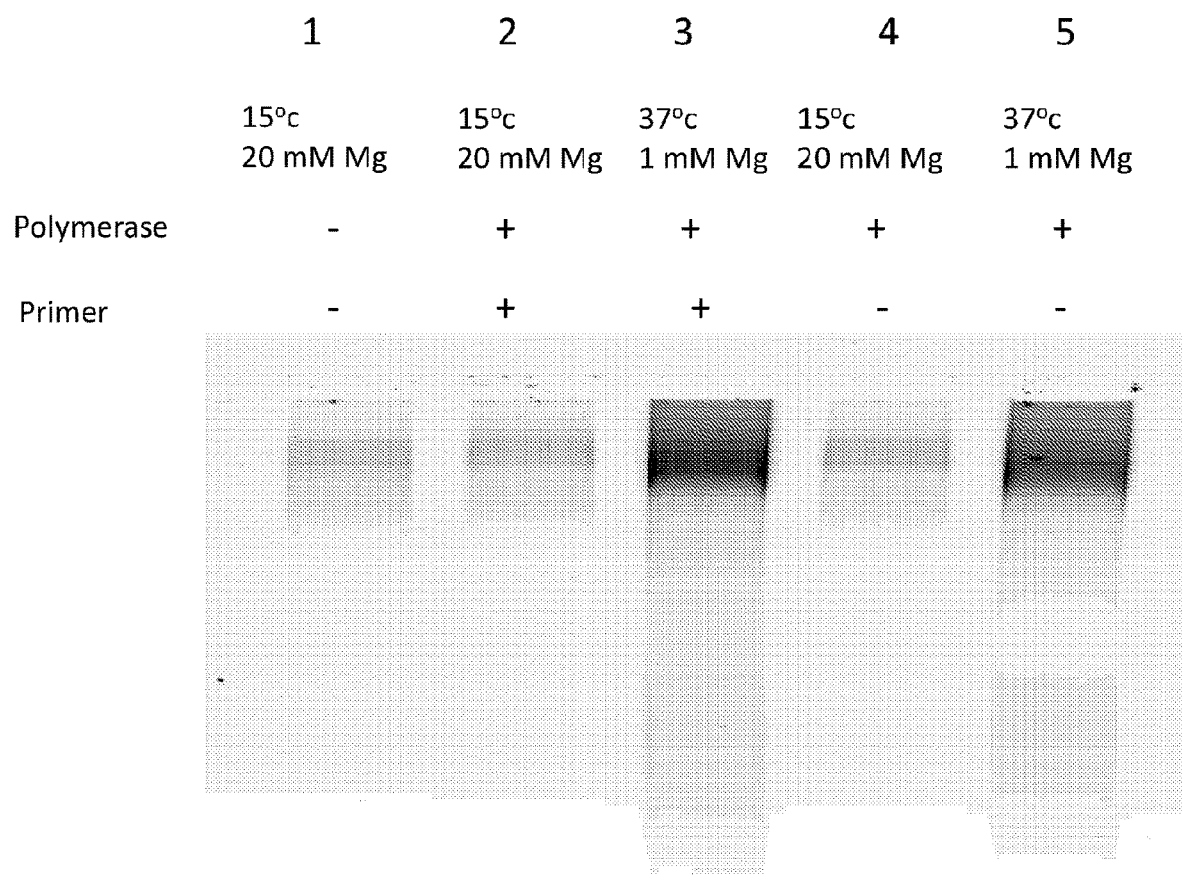

The folding of DNA origami is reversible under intracellular conditions as is demonstrated by increased accessibility to the enzymatic action of the DNA polymerase (FIG. 9). At 15° C., 20 mM Mg+, the nucleic acid origami structure is stable and is not accessible to the enzymatic action of the DNA polymerase (lanes 1, 2 and 4). The structure is destabilized under intracellular conditions, at 37° C. and 1 mM Mg+. As an unstable structure, it is amenable to amplification by the polymerase (lanes 3 and 5).

Example 9: Use of VP2 and VP3 in VLP Formation

VP2 and VP3 are secondary capsid proteins that may increase the efficacy of nucleotide transfer if they are combined with VP1 when forming the VLP. To produce VP2/3 in sufficient quantities for large scale VLP preparation, they are expressed in SF9 cells together with VP1. VP1+VP2 and VP1+VP3 pentamers are extracted and purified in a manner similar to the preparation of VP1 pentamers. VP1+VP2 pentamers and VP1+VP3 pentamers are mixed in a specific ratio of which is determined by standard testing and DNA origami containing VLPs are produced. The VLPs are then used to infect mammalian cells and an increased efficiency of nucleotide transfer is observed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A particle comprising a core and a shell, said core comprising at least one nucleic acid origami structure encapsulated by the shell, said shell comprising at least 12 capsid units, the capsid units comprising one or more capsid proteins from a spherical virus, wherein the particle is a virus-like particle having a quasi-spherical geometry and wherein the core comprising the at least one nucleic acid origami structure is nearly spherical or spherical.

2. The particle of claim 1, wherein the particle has icosahedral geometry.

3. The particle according to claim 1, wherein the diameter of said particle is between 10 and 200 nanometers (nm).

4. The particle according to claim 1, wherein the capsid unit comprises at least five capsid proteins.

5. The particle according to claim 1, wherein each of the capsid units comprises pentamers and/or hexamers of capsid proteins.

6. The particle according to claim 1, wherein the capsid protein is from an artificial source or from a natural source.

7. The particle of claim 1, wherein the viral protein is from a virus of the virus family Polyomaviridae.

8. The particle of claim 7, wherein the viral protein is from a virus selected from the group consisting of: SV40 virus, and human polyomaviruses.

9. The particle of claim 8, wherein the human polyomaviruses are selected from JC virus and BK virus.

10. The particle according to claim 1, wherein the capsid protein is a SV40 virus capsid protein.

11. The particle according to claim 1, wherein the capsid protein is selected from: capsid protein VP1, capsid protein VP2, capsid protein VP3, modified forms thereof native capsid protein and is a functional capsid protein.

12. The particle according to claim 1, wherein said origami structure is encapsulated by at least 72 capsid units.

13. The particle according to claim 1, wherein said capsid unit comprise a combination of viral protein molecules, or modified forms thereof, selected from the group consisting of: 5 VP1 molecules, 5 VP1 molecules and one VP2 molecule, 5 VP1 molecules and one VP3 molecule, and 5 VP1 molecules and one VP2 molecule or one VP3 molecule.

14. The particle according to claim 1, wherein the origami structure is selected from: single stranded DNA, double stranded DNA, single stranded RNA, double stranded RNA, modified nucleic acids, synthetic nucleic acids, or combinations thereof.

15. A method for delivering a nucleic acid molecule into a target cell comprising infecting the cells with the particles of claim 1.

16. The method of claim 15, wherein the target cell is selected from an in vitro cell, or a cell harbored in a tissue or an organism.

17. A composition comprising a plurality of the particles of claim 1.

18. The particle according to claim 3, wherein the diameter of said particle is between 10 and 80 nanometers (nm).

19. The particle according to claim 7, wherein the capsid protein is selected from: capsid protein VP1, capsid protein VP2, capsid protein VP3, modified forms thereof, and a combination thereof, wherein the modified forms of the capsid proteins are functional capsid proteins.

20. The particle according to claim 7, wherein said capsid unit comprise a combination of viral protein molecules, or modified forms thereof, selected from the group consisting of: 5 VP1 molecules, 5 VP1 molecules and one VP2 molecule, 5 VP1 molecules and one VP3 molecule, and 5 VP1 molecules and one VP2 molecule or one VP3 molecule, wherein the modified forms of the viral protein molecules are functional capsid proteins.

* * * * *